United States Patent [19]

Wilbur

[11] Patent Number: 5,679,322
[45] Date of Patent: Oct. 21, 1997

[54] IODINATED BORANE CAGE MOLECULES AS X-RAY CONTRAST MEDIA

[75] Inventor: D. Scott Wilbur, Edmonds, Wash.

[73] Assignee: University of Washington, Seattle, Wash.

[21] Appl. No.: 596,644

[22] Filed: Feb. 5, 1996

Related U.S. Application Data

[62] Division of Ser. No. 107,349, Aug. 16, 1993, Pat. No. 5,489,673.

[51] Int. Cl.⁶ .................................................. A61K 33/18
[52] U.S. Cl. .......................... 424/9.4; 424/9.43; 424/9.44
[58] Field of Search ........................... 424/9.4, 9.43, 424/9.44

[56] References Cited

U.S. PATENT DOCUMENTS

| | | | |
|---|---|---|---|
| 5,256,394 | 10/1993 | Spielvogel et al. | 434/5 |
| 5,272,250 | 12/1993 | Spielvogel et al. | 530/300 |
| 5,280,119 | 1/1994 | Spielvogel et al. | 544/229 |
| 5,286,853 | 2/1994 | Spielvogel et al. | 534/16 |
| 5,455,022 | 10/1995 | Miura et al. | 424/1.61 |
| 5,489,673 | 2/1996 | Wilbur | 536/17.1 |
| 5,545,397 | 8/1996 | Spielvogel et al. | 424/9.4 |

FOREIGN PATENT DOCUMENTS

WO 93/08122  4/1993  WIPO ............... C01B 25/08

OTHER PUBLICATIONS

Jakinek et al., *Collection of Czechoslovak Chemical Communications*, vol. 51, pp. 819–829, 1986.
Sieckhaus et al., *Inorganic Chemistry*, vol. 8, pp. 2452–2457, 1969.
Jelinek et al., *Polyhedron*, vol. 6, pp. 1981–1986, 1987.
Zakharkin et al., *Journal of Organometallic Chemistry*, vol. 267, pp. 81–91, 1984.
Plesek et al., *Polyhedron*, vol. 3, pp. 1351–1355, 1984.
Zakharkin et al., *Journal of Organometallic Chemistry*, vol. 226, pp. 217–222, 1982.
Knoth et al., *Inorganic Chemistry*, vol. 10, pp. 598–605, 1971.
Knoth et al., *Inorganic Chemistry*, vol. 3, pp. 159–167, 1964.
Soloway et al., "Investigation of the Use of $Na_2B_{12}I_{12}$ as an Intravascular Contrast Media," *Angiology*, vol. 15, No. 6, pp. 273–175, Jun. 1964.
Stibr, *Chemical Reviews*, vol. 92, No. 2, pp. 225–250, Apr. 1992.

*Primary Examiner*—John Kight
*Assistant Examiner*—Lara C. Kelley
*Attorney, Agent, or Firm*—Madson & Metcalf

[57] ABSTRACT

Highly iodinated borane and carborane cage molecules, having from 60% to 90% w/w iodine, are disclosed as new and useful X-ray contrast media when combined with a pharmaceutically acceptable carrier. The inclusion of appropriate functional group substituents, such as hydrophilic moieties, increases solubility and lowers toxicity.

25 Claims, No Drawings

IODINATED BORANE CAGE MOLECULES AS X-RAY CONTRAST MEDIA

This application is a divisional of application Ser. No. 08/107,349, filed on Aug. 16, 1993, now U.S. Pat. No. 5,489,673 for IODINATED BORANE CAGE MOLECULES AS X-RAY CONTRAST MEDIA.

BACKGROUND

1. Field of the Invention

The present invention relates to iodinated X-ray contrast media. More particularly, the present invention is directed to periodinated borane and carborane cage molecules for use as diagnostic X-ray contrast media.

2. Technology Review

Over the years, a number of iodinated compounds have been developed and brought to market as X-ray contrast media ("XRCM"). Successful X-ray contrast media share several common characteristics. For example, XRCM must be stable in vivo and must be pharmacologically inert. Other factors also influence effectiveness of XRCM, such as percentage by weight of radiopaque species, e.g. iodine, per molecule, water solubility, and toxicity. The toxicity of the compounds can be related to lipophilicity (hydrophobicity), ionic strength, osmolality, and viscosity.

The above factors are often interrelated. For instance, molecules with increasing numbers of iodine atoms become increasingly more lipophilic, which makes them less water soluble and more likely to be toxic. However, the number of iodine atoms in a single molecule has been shown to have a direct correlation to the clarity of X-ray images obtained. Thus, high iodine content is a desired feature. Iodobenzoic acids were initially used because they had low toxicity; however, fully iodinated benzoic acids were not practical since other functional groups were necessary to give the molecule the desired solubility and pharmacological properties.

Functionalized triiodinated benzene molecules are well known XRCM. In general, it has been necessary to functionalize three of the carbons on the benzene ring for solubilization and detoxification. To obtain more than the usual three iodine atoms on a single molecule, dimers, trimers and polymers of the iodobenzene moiety have been prepared. This has increased the number of iodine atoms, but it also changes the shape of the molecule (to more linear) and increases its viscosity. Increased viscosity causes difficulty in administration and may cause toxicity problems, but dimers have generally been found to be less toxic than the corresponding monomer, presumably due to the decrease in osmolality.

Solubility of the iodinated molecules can be greatly increased by having ionized functionalities on the molecule (e.g. carboxylic acids, amino groups); however, osmolality of the body fluids is affected by the high dosage concentrations needed. High osmolality can cause toxicity. For this reason recent development of X-ray contrast agents has been focused on nonionic, water soluble iodinated compounds.

The functionalized triiodinated benzene-based XRCM that have been brought successfully to market needed very low toxicity because of the large doses required to provide sufficient radiopacity for X-ray contrast. While not wishing to be bound by theory, it is believed that conventional triiodinated benzene-based XRCM simply function as carriers of iodine. Since these conventional X-ray contrast media have from 30% to 70% iodine w/w, dramatic improvements in the contrast obtained in diagnostic X-ray studies may be obtained with contrast agents containing higher percentages of iodine by weight.

It will be appreciated that it would be a significant advancement in the art to provide iodinated diagnostic X-ray contrast media possessing high percentages of iodine by weight, but which also have good solubility and low osmolality.

Such iodinated diagnostic X-ray contrast media are disclosed and claimed herein.

SUMMARY OF THE INVENTION

The present invention is directed to highly iodinated borane cage molecules as new and useful X-ray contrast media. The highly iodinated borane cage compound used in the diagnostic formulations and methods of the present invention have the following general formula:

$$[I_x B^{cm} R_y]^z$$

wherein $B^{cm}$ is a stable borane cage moiety containing from 9 to 12 boron atoms in either a closo- or nido- structure and optionally containing up to 3 carbon atoms as part of the cage structure; I represents iodine atoms of x number substituted on boron atoms of $B^{cm}$ and x is from 6 to 12; R is a substituent of either a boron atom or carbon atom of $B^{cm}$ which contains functional groups that alter the overall charge or solubility of the stable iodinated borane cage compound and y is from 0 to 6; and z represents the overall charge of the stable iodinated borane cage compound ranging from −4 to +4. Inclusion of appropriate functional group substituents, R, is important to increase solubility and lower toxicity.

R is selected from hydrogen, amine, alkyl amine, dialkyl amine, trialkyl amine, carboxylate, alkylcarboxylate, alcohol, alkyl alcohol, ester, alkyl ester, or combinations thereof. In most cases, R is a hydrophilic moiety such as a cyclic heteroalkyl polyalcohol, acyclic heteroalkyl polyalcohol, heterocyclic amino-alcohol, polyhydroxyl group, polyhydroxyalkyl group, or sugar derivative. The substituent R group is attached to the stable iodinated borane cage compound through a boron-carbon, carbon-carbon, boron-nitrogen, carbon-nitrogen, boron-oxygen, or carbon-oxygen bond.

Periodinated and highly iodinated borane and carborane cage molecules within the scope of the present invention can have from 60% to 90% w/w iodine. A diagnostically effective amount of such iodinated borane and carborane molecules may be combined with a pharmaceutically acceptable carrier to form a diagnostic composition for providing X-ray contrast.

DETAILED DESCRIPTION OF THE PREFERRED EMBODIMENTS

The present invention is directed to highly iodinated and periodinated borane and carborane cage molecules as new and useful X-ray contrast media.

Borane Structures. Although many boranes are unstable towards hydrolysis, some boron hydrides form very stable cage molecules. Using molecular orbital calculations similar to the "Huckel rule" for aromatic compounds (4n+2 electrons), boranes and heteroboranes in deltahedral cages with 2n+2 (n=6–12) boron valence electrons are predicted to form very stable, highly delocalized, closed cage (closo) species. This stability is particularly evident in the fact that neutral decaborane $B_{10}H_{10}$, and dodecaborane, $B_{12}H_{12}$, have not been isolated, but the dianions $B_{10}H_{10}^{2-}$ and $B_{12}H_{12}^{2-}$, with 2 electrons in excess, are readily isolated and are very stable cage molecules. For borane cages containing carbon atoms, one of the requisite excess electrons is provided by the carbon atom. Thus, the monocarbon carborane $CB_{11}H_{12}^{-}$ is stable as is the neutral dicarbaborane cage molecule $C_2B_{10}H_{12}$.

Representations of the cage structures and the accepted numbering system for unsubstituted bicapped square antiprism decaborane ($B_{10}H_{10}^{2-}$, 1) and icosahedral dodecaborane ($B_{12}H_{12}^{2-}$, 2) are shown below with the cage protons left off to simplify structures. Both of these compounds can be purchased from a commercial source (Boron Biologics, Raleigh, N.C.). In addition, several procedures for the synthesis of 1 and 2 have been described in the literature. Barton L., "Dodecahydrododecaborates," in *GMELIN Handbook of Inorganic Chemistry, Boron, 8th Edition, 2nd Supplement*, Niedenzu K., Ed., vol. 1, 2.13.1, pp. 195–196 (1983); Barton L., "Dodecaborane Species," in *GMELIN Handbook of Inorganic Chemistry, Boron, 3rd supplement*, Fluke E., Ed., vol. 1, 2.14, pp. 222–229 (1987); Makhlouf et al., "Practical Synthesis for Decahydrodecaborates," *Inorganic Chemistry*, vol. 6, pp. 1196–1198 (1967); and Miller et al., "Borane Anions," *Inorganic Synthesis*, vol. 10, pp. 81–91 (1967). Decaboranes and dodecaboranes are air and moisture stable, thermally stable, and resistant to degradation by acids, bases, and mild oxidizing reagents.

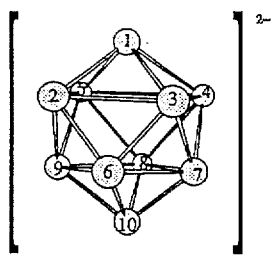

unsubstituted
decaborane
1

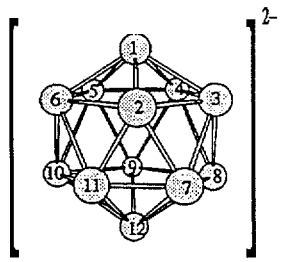

unsubstituted
dodecaborane
1

Monocarbaboranes. A number of monocarbon carboranes can be synthesized following literature reports. Rudolph, R. W., "Boranes and Heteroboranes: A Paradigm for the Electron Requirements of Clusters?" *Acc. Chem. Res.*, vol. 9, pp. 446–452 (1976); Williams, R. E., "Carboranes," *Progress in Boron Chemistry*, Brotherton, R. J. and Steinberg, H., Eds., vol. 2, pp. 37–118 (1970); and B. Stibr, "Carboranes other than $C_2B_{10}H_{12}$," *Chem. Rev.*, vol. 92, pp. 225–250 (1992). The currently preferred carborane cage for use in the present invention is closo-$CB_{11}H_{11}R^{1-}$ because it has a very stable icosahedral structure and because it has 11 boron atoms for iodine substitution. Two general methods of producing monocarbon carboranes involve reaction of decaborane ($B_{10}H_{14}$) with alkyl isocyanides or sodium cyanide, with the sodium cyanide reaction being currently preferred.

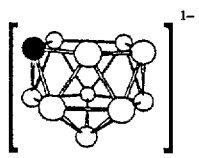

nido-monocarbaborane
49

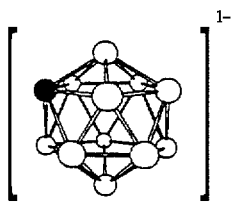

closo-monocarbaborane
50

Dicarbaboranes. Carboranes which contain two carbon atoms ($C_2B_{10}H_{12}$) form nearly icosahedral geometry cage structures, similar to that of dodecaborane ($B_{12}H_{12}^{2-}$). The atom numbering system is the same as that of the icosahedral dodecaborane shown above, with the numbering beginning with C(1). The position of the two carbons in carborane cages can vary from the 1,2-(ortho-), 3a, 1,7-(meta-), 3b, or 1,12-(para-), 3c, as depicted below (darker circles are carbon atoms, with the cage protons omitted to simplify structures). Carboranes are readily prepared and have a high chemical and thermal stability. Carboranes are resistant to degradation by acids, weaker bases, and air oxidation. As with the borane cages, there appears to be extensive delocalization of electrons. The ortho-isomer has a larger dipole moment with more positive (charge) character on the carbon atoms than the other isomers, lending to some unique chemistry of substituents attached to the carbon atoms in that isomer. For example, the protons on the carbon atoms in the ortho-isomer are more acidic, undergo metallation more readily, and have a greater electron withdrawing effect for substituents attached to the cage carbon atoms than in the other two positional isomers.

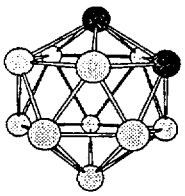

(ortho) 1,2-carborane
3a

-continued

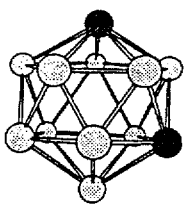

(meta) 1,7-carborane
3b

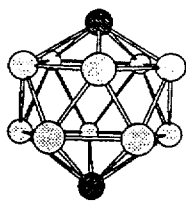

(para) 1,12-carborane
3c

Closo-carborane cages are extremely lipophilic in nature but may be degraded with strong base or amines (e.g. pyrrolidine) to form the nido-carborane which has one boron atom removed, $C_2B_9H_{12}$, 4, as depicted below. The relative ease of removing one of the boron atoms of the cage structure is in the order of ortho>meta>para. The anion formed is water soluble.

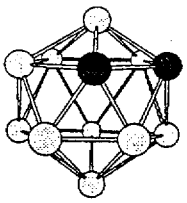

closo-1, 2-carborane
3a

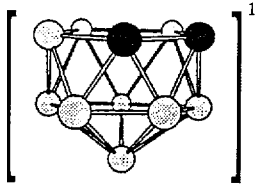

nido-1,2-carborane
4

Borane and Carborane Iodination. Boron cage molecules and carborane cage molecules undergo electrophilic substitution reactions with iodine to convert B-H to B-I bonds. The boron-iodine bond formed is thermodynamically more stable than carbon-iodine bonds with bonding strengths of 91 kcal/mol for B-I, 53 kcal/mol for R-CH$_2$-I and 64 kcal/mol for Benzene-I, "Bond Strengths of Diatomic Molecules/Bond Strengths of Some Organic Molecules" (1982) In *CRC Handbook of Chemistry and Physics*, Weast R. C. and Astle M. J., Eds., 63rd Edition, pp. F-186 and F-205.

Stability of iodo-compounds is not only dependent on bond strength, but also on resistance to displacement reactions such as nucleophilic substitution reactions. Substitution reactions generally occur by SN1, SN2, or SNAr processes. Since the B-I bond is very strong and the resulting ion cannot be stabilized by the cage structure, it is unlikely that an SN1 process will occur on a borane or carborane cage molecule. Further, SN2 and SNAr reactions occur by "backside attack" which should be impossible in the cage structures. Also, because of the structure and bond strengths it is unlikely that enzymes in the body will readily remove the iodine in vivo.

The closo-boranes $B_{10}H_{10}^{2-}$, 1, and $B_{12}H_{12}^{2-}$, 2, react in aqueous or alcoholic solutions with $Cl_2$, $Br_2$, $I_2$, ICl, and N-chlorosuccinimide to give halogenated derivatives. W. H. Knoth et al., "Chemistry of Boranes IX. Halogenation of $B_{10}H_{10}^{-2}$ and $B_{12}H_{12}^{-2}$," *Inorganic Chemistry*, vol 3, pp. 159–167, (1964) and Klanberg and Muetterties, "Chemistry of Boranes. XXVII. New Polyhedral Borane Anions, $B_9H_9^{2-}$ and $B_{11}H_{11}^{2-}$," *Inorganic Chemistry*, vol. 5, pp. 2452–2457, (1969). Initial reactions with dihalides is extremely rapid but decreases as the halogenation process proceeds. A mixture of halogenated compounds is obtained unless sufficient reagent/conditions are provided for perhalogenation. Methods for periodination of compounds 1 and 2 are described in W. H. Knoth et al., "Chemistry of Boranes. IX. Halogenation of $B_{10}H_{10}^{-2}$ and $B_{12}H_{12}^{-2}$," *Inorganic Chemistry*, vol. 3, pp. 159–167, (1964).

Halogenated derivatives of 1 and 2 are stable to air and moisture and have no special handling requirements. The anionic iodinated species are water soluble, but can be precipitated by preparing the salts of large univalent cations such as Cs or tetramethylammonium ions. Purification can be accomplished by recrystallization of the precipitated salts from water or aqueous organic solvent mixtures. Conversion of the insoluble salts to soluble acid form or alkali metal salts (e.g. Na) can be readily accomplished by passing them over ion exchange resins (e.g. Amberlite IR-120).

All of the halogenated derivatives of 1 and 2 are "exceedingly stable." W. H. Knoth et al., "Chemistry of Boranes. IX. Halogenation of $B_{10}H_{10}^{-2}$ and $B_{12}H_{12}^{-2}$," *Inorganic Chemistry*, vol. 3, pp. 159–167, (1964). Samples of the compounds resisted attack by strong acid, aqueous sodium hydroxide, refluxing methanolic sodium methoxide, potassium amide/liquid ammonia solutions, sodium acetylide in liquid ammonia, and Grignard reagents in refluxing tetrahydrofuran. Importantly, the iodinated species $B_{12}I_{12}^{2-}$ was found to be resistant to degradation on treatment with chlorine, 20% aqueous sodium hydroxide at 85° C., and sulfuric acid at 150° C.

Iodination of carboranes is more difficult. Although iodination can be accomplished at the carbon atoms, the resultant iodine atoms are unstable toward nucleophiles and reduction (ortho<meta<para). Therefore, the present invention is directed to iodination of the cage boron atoms. Because closo-carboranes are very lipophilic, water solubilizing substituents are attached to the carbon atoms in the present invention, rather than iodine atoms.

Halogenation of cage boron atoms in closo-carboranes has been studied previously. While perfluorination and perchlorination of dicarbaboranes have been obtained, (Kongpricha S. and Schroeder H., "Icosahedral Carboranes. XII. Direct Fluorination of o-, m-, and p-Carborane," *Inorganic Chemistry*, vol. 8, pp. 2449–2452 (1969) and Schroeder H., et al., "A New Series of Organoboranes. II. The Chlorination of 1,2-Dicarbaclovododecaborane," *Inorganic Chemistry*, vol. 6, pp. 1092–1096 (1963)), perhalogenation of bromine or iodine has not been accomplished. Indeed, the literature reports that a maximum of 3 bromine atoms can be substituted onto ortho-carborane using AlCl₃ catalyst unless the carbons have an electron donating alkyl substituent (e.g. methyl group) which increases the amount of substitution by 1 to a maximum of 4 bromine atoms. With meta-carborane and para-carborane only the mono- and di-bromo or di-iodo derivatives could be obtained under the reaction and conditions studied, Sieckhaus J. F., et al., "Icosahedral Carboranes. XIII. Halogenation of p-Carborane," *Inorganic Chemistry*, vol. 8, pp. 2452–2457 (1969) and Zakharkin L. I., et al., "Electrophilic Monohalogenation of o- and m-Carboranes by Iodine and Bromine in the Presence of AlCl₃ in Polychloromethanes," *Journal of General Chemistry USSR*, vol. 57, pp. 1800–1803 (1987).

In contrast to the closo-dicarbaboranes, it has been reported that closo-(monocarbon)-carbaboranes do not readily perhalogenate even with chlorine. Indeed, an early study reported that reaction of the unsubstituted anionic monocarbon carborane with chlorine gas at 0° C. caused extensive degradation of the carborane molecule and stated that attempts to iodinate C-trialkylamine derivatives, "even with the aid of AlCl₃ or a photolamp", were unsuccessful. Hyatt D. E., et al., "Monocarbon Carboranes. I. Syntheses and Reactions of the $B_{10}H_{12}CH^-$ and $B_{10}H_{10}CH^-$ Ions and their C-Trialkylamine Derivatives," *Inorganic Chemistry*, vol. 6, pp. 2229–2233 (1967). A later study, however, reported that the hexachloro derivative was obtained when the unsubstituted monocarbon carborane is chlorinated with excess chlorine in acetic acid at 80° C. Jalinek T., et al., "Chemistry of Compounds with the 1-Carba-closo-Dodecaborane Framework," *Coll. Czech. Chem. Commun.*, vol. 51, pp. 819–829 (1986). The hexabromo derivative was obtained under the same reaction conditions, whereas only the di-iodo derivative is obtained when excess iodine is used.

Borane Substituent Chemistry. Unsubstituted periodinated decaborane and dodecaborane may be used as XRCM within the scope of the present invention since they are water soluble anions similar to the relatively nontoxic thiododecaborate (BSH) presently under study for boron neutron capture therapy (BNCT). However, substituents will likely be needed on iodinated borane cage molecules and on iodinated carborane molecules to obtain the desired aqueous solubility and pharmacological properties.

A number of different substitution reactions are known to occur with the closo-borate dianions, $B_{10}H_{10}^{2-}$ and $B_{12}H_{12}^{2-}$, without degradation of the borane cage. Generalized outlines of some of the known substitution reactions are shown in the chemical reaction schemes below (n=10 or 12 and the counterions are not shown). Reactions such as carbonylation with carbon monoxide, acyl derivative formation from acid chlorides, diazonium salt formation and reactions, amination with hydroxylamine-O-sulfonic acid, and ether formation with primary and secondary alcohols, have been reported. Symmetrical disubstituted products are shown below, but monosubstitution and nonsymmetrical disubstitution products are also readily obtained.

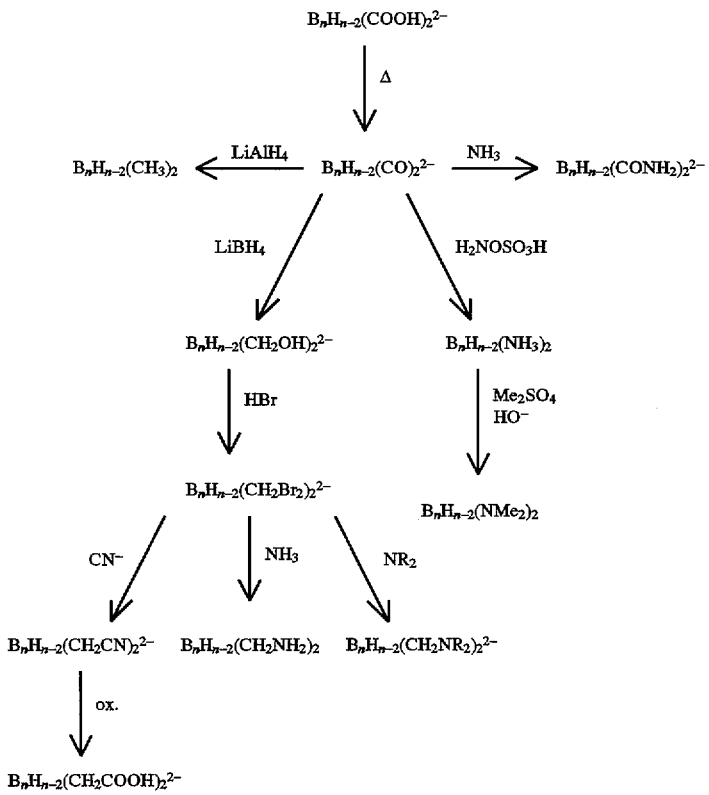

Two types of boron atoms exist in the $B_{10}H_{10}^{2-}$ cage structure: those bonded to five other atoms (apical boron atoms, atoms numbered 1 and 10) and those bonded to six other atoms (equatorial boron atoms). Some reactions give preferential substitution at the apical positions while other reactions give preferential equatorial substitution. All of the boron atoms in $B_{12}H_{12}^{2-}$ are equivalent (bonded to six other atoms). For the disubstituted products, substitution is primarily at 1,12-positions of $B_{12}H_{12}^{2-}$ with a minor product being the 1,7 disubstitution.

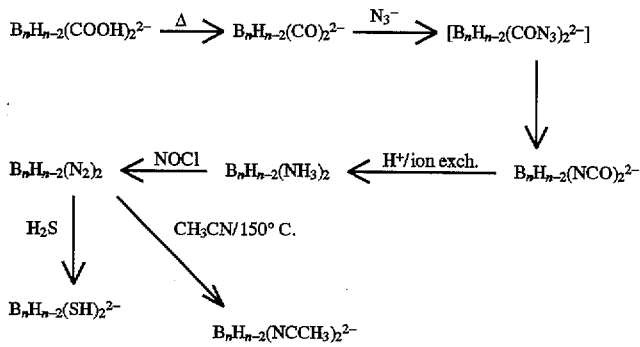

Dicarbaborane Derivatives. Carborane cage moieties are also resistant to most reaction conditions, such that different types of chemistry may be carried out without cage degradation. Unsubstituted ortho-carborane can be obtained from commercial sources (Aldrich). Generally, ortho-carboranes can be prepared from the reaction of moisture sensitive decaborane ($B_{10}H_{14}$, arachno-configuration) with alkynes as depicted below (shown in conventional 2D representation).

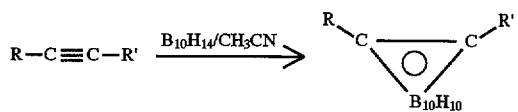

Substituents on carboranes can be attached to either the cage carbon atoms or boron atoms, or both. Monosubstituted ortho-carboranes can readily be prepared from reactions of decaborane with appropriately substituted alkynes or they may be prepared from metallation reactions of carborane followed by metal/halogen exchange reactions.

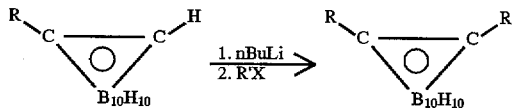

Disubstitution with identical substituents can be accomplished by reaction of bis-metallated unsubstituted carborane with excess quantities of halogenated reagents. Water solubilizing substituents according to the present invention are attached to the carbon atoms to maximize the number of B-I bonds that can be made virtually any organic group can be attached to the cage carbons using the usual carbon-carbon bond forming reactions (e.g. metallation/halogen exchange).

Due to the electronic and steric nature of the carborane cage, some chemistry does not occur in the usual manner on the carbon alpha to carborane cage carbons. But, the chemistry becomes more "normal" when there are one or more atoms between the cage and the atom undergoing the reaction. There is less of an effect on the chemistry of the adjacent carbons when the cage carbons are in the meta- or para-isomeric positions (Compounds 3b and 3c).

It has been found that the closo-1,2-carborane is easily degraded to the nido-1,2-carborane. Although the nido compound may be iodinated, it would result in a 1-charge on the ring. Therefore, the 1,7-carborane is preferred where a neutral closo compound is desired. The closo-1,7-carborane is not readily degraded with amines such that the amine derivative is a good intermediate compound for the preparation of substituted 1,7-carborane compounds. A synthetic scheme for preparing aminomethyl-1,7-carborane, 72, is shown below (cage protons are omitted for simplicity). Reaction of 72 with an amine reactive hydrophilic moiety should provide a water soluble compound. The corresponding diamino compound may be prepared by the below synthesis, except that two equivalents of reagents are used, and the trimethylsilyl group is not used.

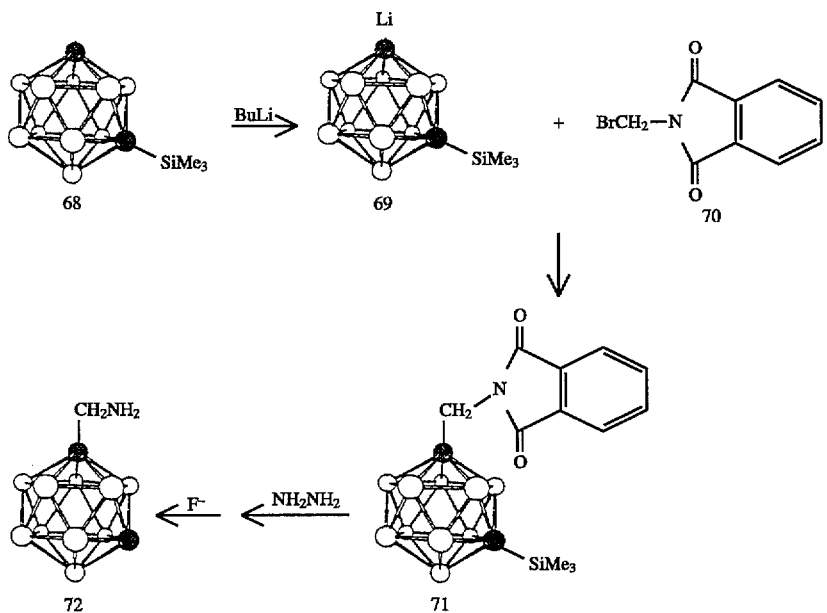

The preparation of the carboxylic acid derivative of 1,7-carborane is shown below (cage protons are omitted for simplicity). Once formed, the carboxylic acid can be activated by preparation of the tetrafluorophenyl ester. Iodination and conjugation with a hydrophilic moiety, such as glucamine, results in compound 86, which is neutral and water soluble. The dicarboxylate diester can be prepared in an analogous manner and used to prepare compound 88.

Monocarbaborane Derivatives. The synthesis of C-amino derivatives of the monocarbaborane $1\text{-}CB_{11}H_{12}^{1-}$ are prepared by two separate routes, illustrated below with the cage protons and formal charges (of neutral compounds) omitted to simplify structures. According to the first route, reaction of decaborane (44, $B_{10}H_{14}$, an arachno compound) with sodium cyanide in water yields nido-aminocarborane 45. Aminocarborane 45 can be isolated and converted to the

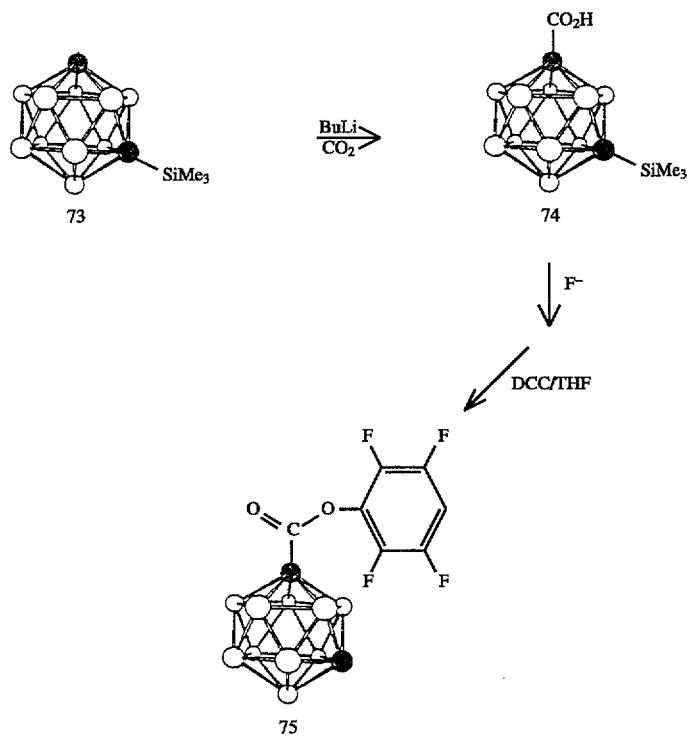

trimethyl derivative 46 by reaction with dimethylsulfate in aqueous sodium hydroxide or both reaction steps can be accomplished prior to isolation of 46. The trimethyl derivative 46 can also be prepared by a second, higher yielding, route as described in Example 3.

A boron insertion reaction may be used to form the closo-monocarbon carborane 50 from the nido-carborane 46. This reaction can either be carried out in the presence of the trimethylamine group or after removal of the trimethylamino group using Na in THF. Reaction of trimethylaminonido-carborane 46 with triethylaminoborane at 200° C. results in insertion of the boron, but this is accompanied by loss of a methyl group on the amine to yield dimethylamino-closo-carborane 47. To obtain the unsubstituted closo-carborane 50, the dimethylamino group must be converted back to a trimethylamino group to form 48. This may be accomplished with dimethylsulfate and base.

Neutral monocarbon carborane derivatives may be prepared at reaction sites other than the tertiary amine. For instance, it is believed a primary amine derivative of the dimethylaminocarborane 47 may be modified at that site, as shown below. The cage protons and formal charges have been omitted to simplify structures.

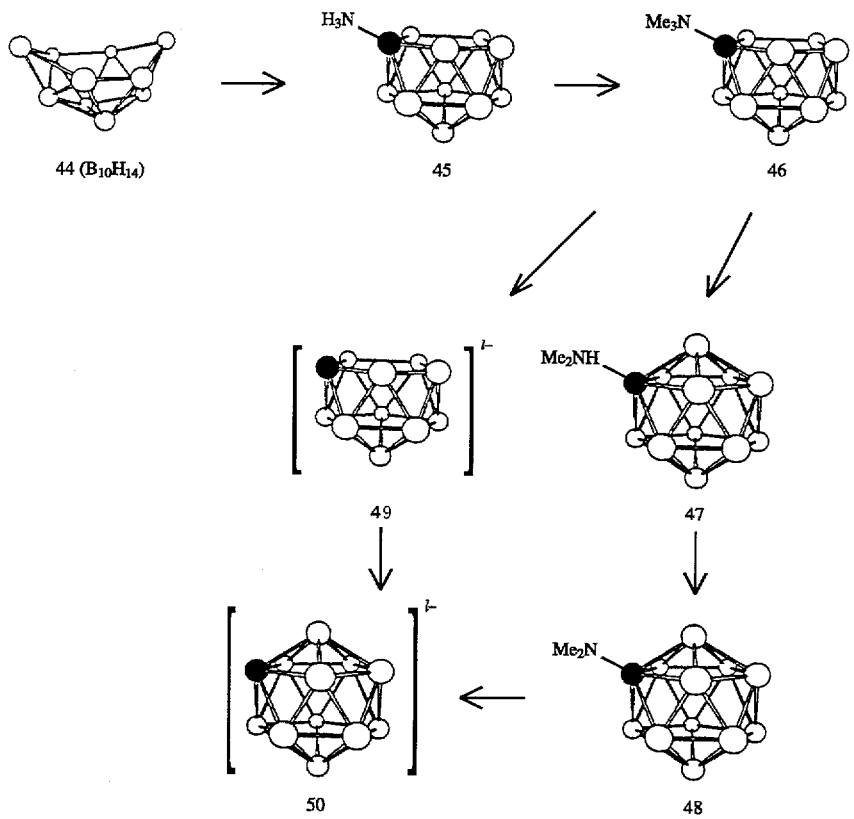

The tertiary amine derivatives of monocarboranes are neutral and with appropriate hydrophilic substituents, water soluble compounds may be prepared. The amine functionality of compound 47 may alkylated for derivatization. Demethylation and derivatization of the dimethylaminocarborane 47 may also be used to prepare useful derivatives. Plesek, J., et al., "Unusual Demethylation of 1-Dimethylamine-1-Carba-closo-Dodecaborane," *Polyhedron*, vol. 3, pp. 1351–1355 (1984).

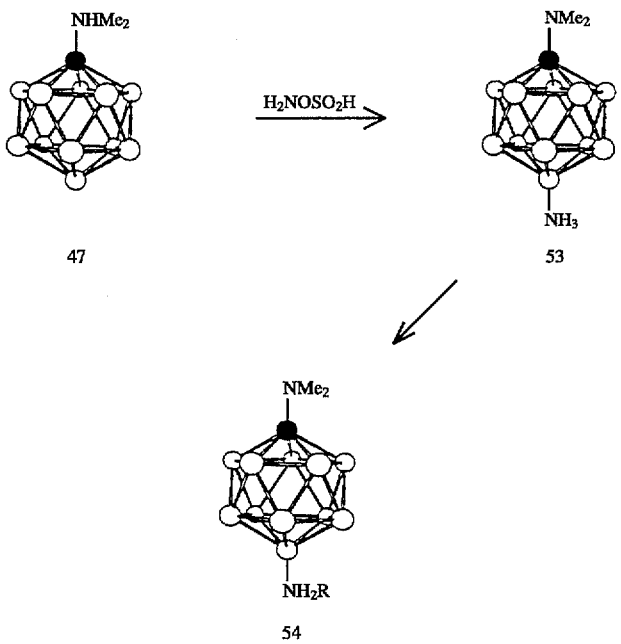

The unsubstituted carborane may be derivatized by amination and subsequent alkylation of the amine (Jelinek, T., et al., "Some Electrophilic Reactions of closo-[1-$CB_{11}H_{12}$]- and One-Boron Insertion into nido-7-L-7-$CB_{10}H_{12}$ (L=H- or $Me_3N$) Compounds. Isolation of all Three B-Substituted closo-$Me_3$N-1-$CB_{11}H_{11}$ Derivatives," Polyhedron, vol. 6, pp. 1981–1986 (1987)), as well as lithiation and alkylation of the carbon (Knoth, W. H., "$B_{10}H_{12}CNH_3$, $B_9H_9CH^-$, $B_{11}H_{11}CH^-$, and metallomonocarboranes," Inorganic Chemistry, vol 10, pp. 598–605 (1971)), as shown below. The cage protons and formal charges have been omitted to simplify structures.

iodine may be required in some cases to provide better solubilization or derivatization for detoxification. For the compounds of the present invention to be functionally competitive with existing iodinated phenyl derivatives, the highly iodinated boron cage molecules should have a minimum of 6 iodine, and preferably 8 to 10 iodines atoms per molecule.

In general, boron substitution is accomplished by Friedel-Crafts electrophilic aromatic substitution-type reactions, where $AlCl_3$ catalyst is used. In the sequence of reactions shown below, 9-B-alkylation can be obtained by reaction of ortho-carborane with alkyl halides/$AlCl_3$ as described by

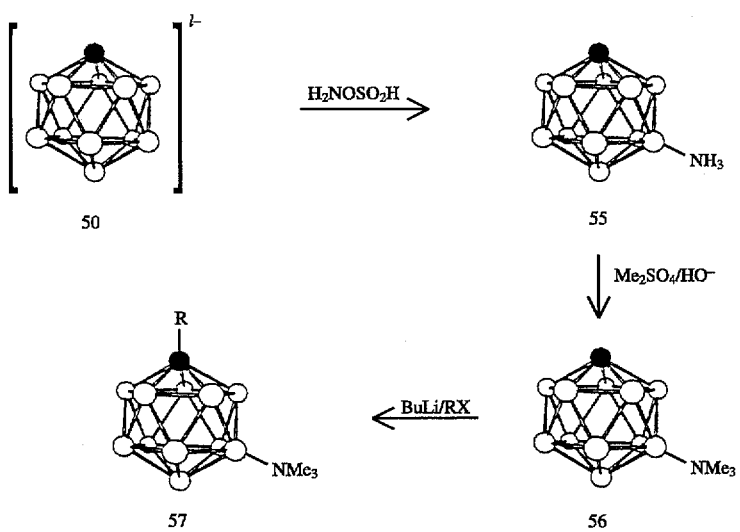

Iodination. The compounds within the scope of the present invention are preferably highly iodinated or periodinated on the boron atoms; however substituents other than Zakharkin et al., "Synthesis of B-Organo-Substituted 1,2-, 1,7-, and 1,12-Dicarbaclosododecaboranes," Journal of Organometallic Chemistry, vol. 226, pp.217–222, (1982).

Oxidation of the B-alkyl compound with $CrO_3$ yields the B-COOH derivative. Zakharkin et al., "Synthesis of σ-(o-Carboran-9-yl) and σ-(m-Carboran-9-yl)-π-cyclopentadienyl-dicarbonyliron and their Rearrangement in Reactions with Bromine to π-(o-Carboran-9-yl) cyclopentadienyl-and π-(m-Carboran-9-yl) cyclopentadienyl-Dicarbonyliron Bromides, Respectively," *Journal of Organometallic Chemistry*, vol 267, pp. 81–91 (1984). The B-COOH formed are very acidic, but the electron withdrawing properties of iodine atoms on the periodinated carborane make the acid ionizable at physiological pH. Therefore, it is believed that a B-COOH may assist in solubilization and in obtaining preferential kidney excretion. To obtain other compounds, derivatization of the B-substituted acid chloride with amines may be possible without degradation of the carborane ring.

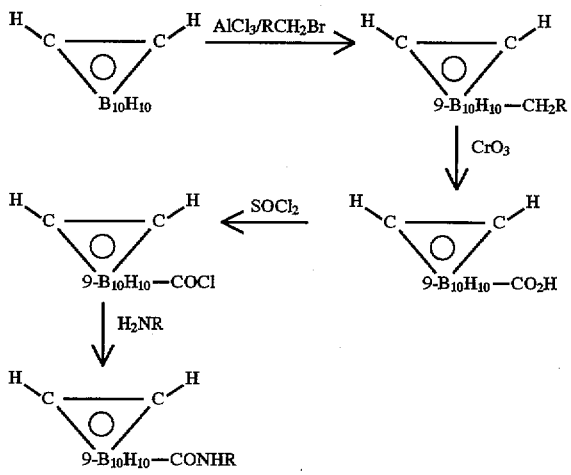

A boron-insertion reaction into the dicarbollide (dianion) of ortho-carborane may also be used to obtain B-substituents. In this reaction the base degraded nido-carborane 4 is reacted with strong base (NaH or nBuLi) to deprotonate the anion and form the dicarbollide ion. This ion reacts with ethyl or phenyl boron dichlorides as depicted in FIG. 9 to reform the closo-carborane. B-Cl and B-Br insertion products have been formed from this reaction, Roscoe et al., "Icosahedral Carboranes. XIV. Preparation of Boron-Substituted Carboranes by Boron-Insertion Reaction," *Inorganic Chemistry*, vol. 9, pp. 1561–1563, (1970) and J. Li et al., "A Simple synthesis of 3-Bromo-o-carborane," *Inorganic Chemistry*, vol. 29, pp. 4162–4163 (1990), but no B-I insertions have been reported.

Iodination of Carboranes. The iodination methods of the present invention increase the level of substitution over the methods previously reported in the literature. Strong acid catalysts, such as concentration $H_2SO_4$ and triflic acid are preferably used to provide high electrophilic catalytic activity.

Ortho- and meta-carboranes were iodinated by reaction with a 1:1 mixture of ICl and tetrachloroethane, heated to 150° C. After several days reaction mixtures were obtained, which by mass spectral analysis indicated that the highest substitution in each case was 6 iodine atoms. However, it was found that these reaction conditions could be used to prepare periodinated monocarbon carborane 50, and the corresponding C-amino monocarbon carborane. N,N-Dimethyl-amino-1-(monocarbon)-carborane 47 was also periodinated, but a mixture of 2 compounds was obtained (1:3 ratio by HPLC).

Triflic acid catalyst is used in the reaction of 1-dimethylamine-1-carba-closo-dodecaborane(12) in ICl at room temperature to cleanly yield the 1-dimethylamine-7,8,9,10,11,12-hexa-B-iodo-1-carba-closo-dodecaborane(12), 47.

Attempts to periodinate ortho-carborane and meta-carborane were conducted at elevated reaction temperatures (120° C.) with a 1:1 v/v mixture of triflic acid and ICl. The reactions were followed by HPLC analysis showing that over a 5 to 6 day period many different peaks grew in a disappeared as the iodination progressed. After 6 days very little change was noted in HPLC. The spectral data of the isolated products from reactions of the ortho- and meta-carboranes indicated that 8 (not 10) iodine atoms had been substituted on the cage. This result suggests that the two boron atoms in each structure which are connected to two carbon atoms (boron atoms at positions 3 and 6 in ortho-carborane and at 2 and 3 in meta-carborane, as shown below, with iodine atoms omitted for simplicity) were extremely resistant to iodine substitution. This was understandable as those are the two most electron deficient boron atoms. However, HPLC analyses of the iodinated ortho- and meta-carborane reaction mixtures showed that in each example there was a more lipophilic compound produced in a small percentage, which is likely to be that of the periodinated (e.g. having 10 iodine atoms) ortho- and meta-carborane. This suggests that the periodinated compounds may be obtained using the described reaction conditions over more extended reaction periods (e.g. months).

Based on these results, periodination of para-carborane is anticipated under the same reaction conditions, as all boron atoms only have one carbon attached. Indeed, reaction of para-carborane under the same reaction conditions resulted in obtaining a substitution of 12 iodine atoms, where 2 of the iodine atoms were present on the cage carbon atoms. This full substitution gave only one peak by $^{11}B$ NMR in THF, but two peaks were observed by $^{11}B$ NMR when base

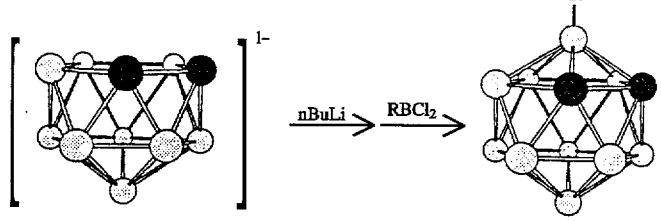

4

(NaOH) was added, indicating that one of the iodine atoms on the carbons had been removed. FAB⁻ mass spectral analysis indicated that there were 11 iodine atoms on the molecule, but the twelfth one would be expected to be removed under conditions of analysis.

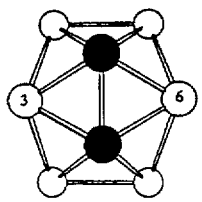

ortho-carborane

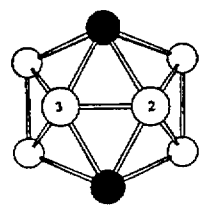

meta-carborane

Iodinated XRCM of the Present Invention. To be successful XRCM, the iodinated molecules within the scope of the present invention must have high water solubility and have low toxicity in high doses. While much is known about the structure-activity relationships of many functional groups for triiodinated benzene-based contrast agents, little is currently known about what effects different substituents will have on solubility or toxicity of the periodinated borane or carborane cage molecules. However, it is presently believed that substituents which have been successfully used with triiodinated benzene compounds will also work for the iodinated boranes and carboranes.

While much of the more recent research in development of contrast agents has been directed at obtaining nonionic molecules, the periodinated boranes and carboranes are quite different from the triiodinated benzene compounds and it is believed that low toxicity may be obtained for ionic species of the cage molecules. Therefore, both ionic (including zwitterionic) and nonionic molecules are included within the scope of the present invention.

The ionic and zwitterionic compounds of the present invention are preferably derivatives of dodecaborane 2, since there are more iodine atoms per molecule possible with dodecaborane than decaborane, the dicarbonylated derivative of dodecaborane is more hydrophilic than the corresponding dicarbonyl decaborane, and a large number of substitution reactions are available. Ionic and zwitter-ionic compounds of the present invention preferably have an overall formal charge ranging from mono-anionic to mono-cationic. More highly charged species, up to a net ±4 charge are also included within the scope of the present invention.

Shown below are the chemical structures of six periodinated disubstituted dodecaborane compounds, $B_{12}I_{12}^{2-}$ 5, $B_{12}I_{10}(CH_2NHCOCH_3)_2^{2-}$ 6, $B_{12}I_{10}(CH_2NMe_2)_2^{2-}$ 7, $B_{12}I_{10}(CH_2CO_2H)_2^{2-}$ 8, $B_{12}I_{10}C_{10}N_2O_7H_{23}^{1-}$ 78, and $B_{12}I_{10}N_2O_{10}H_{24}$ 80, within the scope of the present invention (cage iodine atoms and formal charges are omitted to simplify structures). Because it is a goal of the present invention to have a high iodine percentage in the molecule, substituents containing a small number of atoms are illustrated to keep the percentage of iodine as high as possible. The particular substituents chosen affect the overall formal charge on the molecule. The fully iodinated dodecaborate 5 and bis-acetylmethylamino derivative, 6, have a formal charge of −2; the bis-dimethylamino derivative, 7, exists as a neutral di-zwitterionic species; the bis-carboxymethyl derivative, 8, is deprotonated at physiological pH and has a formal −4 charge; the trimethyl amino glucoheptonyl derivative, 78, has a formal charge of −1; and compound 80 is neutral.

Based on previous studies, the ionic nature of the compounds is likely to make them water soluble. It is expected that for these compounds the aqueous solubility will be primarily a function of the counterion used.

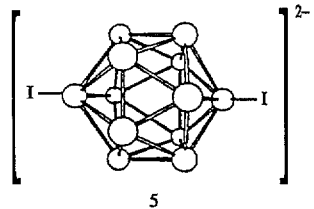

5

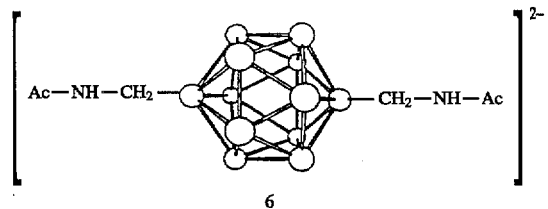

6

-continued
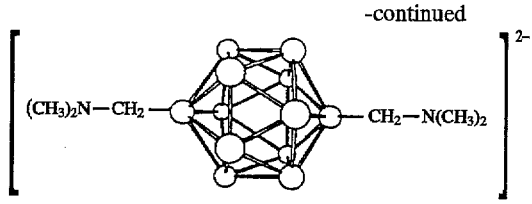
7
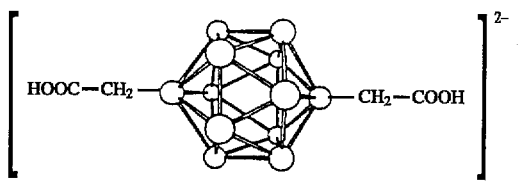
8
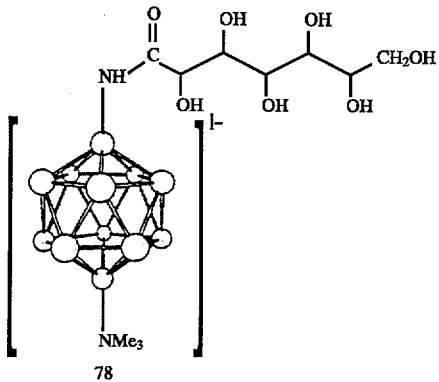
78
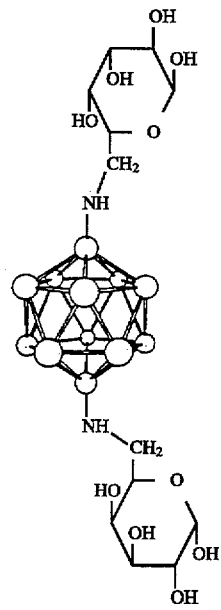
80
Shown below are the chemical structures of three periodinated monosubstituted dodecaborane compounds, $B_{12}I_{11}NHCH_2COOH$ 76, $B_{12}I_{11}C_6NO_5H_{13}$ 77, $B_{12}I_{11}C_8N_2O_6H_{18}$ 79, within the scope of the present invention (cage iodine atoms and formal charges are omitted to simplify structures).

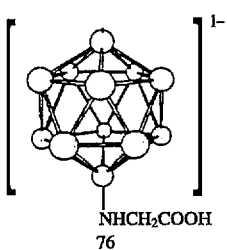

76

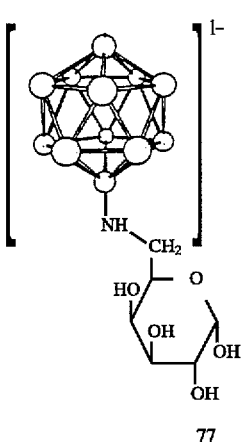

77

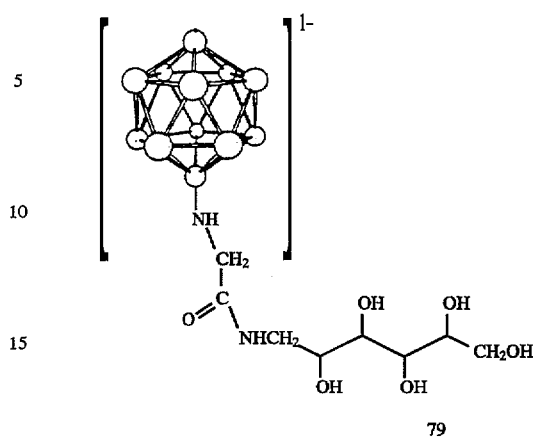

79

Nonionic ortho-dicarborane derivatives 9, 10, and 11 contain polyhydroxyl functional groups to aid in solubilization. The functional groups preferably are not ionized in vivo. Maurer et al., "Hydrophilically Augmented Glycosyl Carborane Derivatives for Incorporation in Anti-body Conjugation Reagents," *Organometallics*, vol. 7, pp. 2519–2524, (1988), report that glycosylated carboranes "showed a surprising water solubility", thus it is expected that the mono-glucosamine derivative, 9, and diglucosamine derivative, 10, are water soluble. It is also expected that the bis-dihydroxypropylcarborane 11 i also water soluble. Those skilled in the art will appreciate that other nonionic derivatives of periodinated ortho-dicarborane may be prepared by using other hydrophilic moieties in the place of the glucosamine or dihydroxypropyl groups.

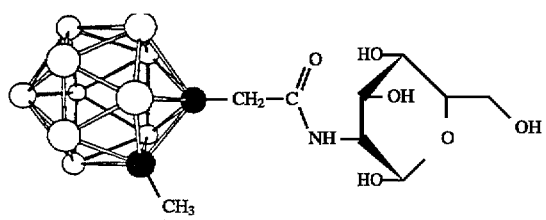

9

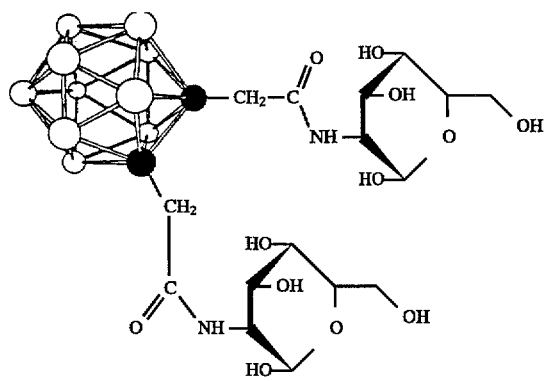

10

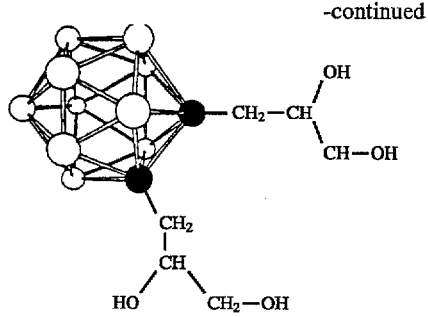
Nonionic meta-dicarborane derivatives 85, 86, 87, and 88 contain polyhydroxyl functional groups to aid in solubility. The cage iodine atoms have been omitted to simplify structures.
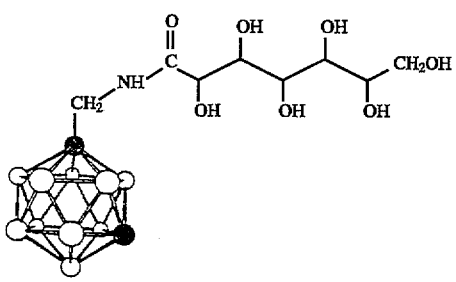
85
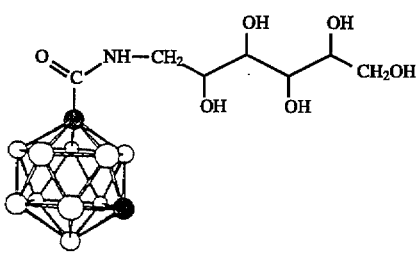
86
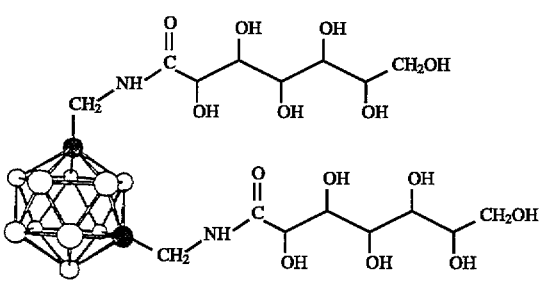
87
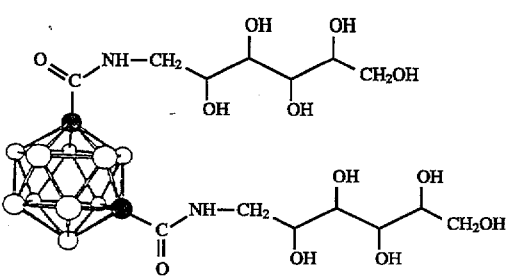
88

Several monocarbon carborane compounds, 51, 52, 81, 82, 83, and 84 are shown below (cage iodine atoms and formal charges are omitted for structure simplicity).

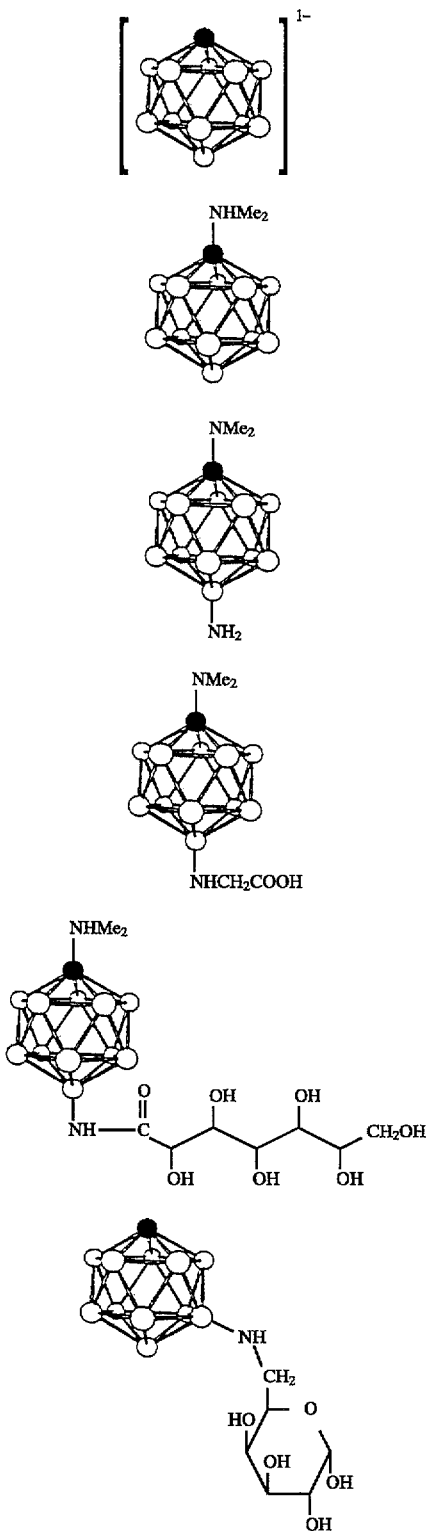

Hydrophilic moieties are used to solubilize the highly iodinated carboranes. As used herein, hydrophilic moieties include molecules with a high affinity for water such that log p<0, where p is the partition coefficient between octanol and water (the molecule's concentration in the octanol phase divided by the molecule's concentration in the water phase).

Typical hydrophilic moieties within the scope of the present invention include heterocyclic amino-alcohols such as dihydroxypyrrolidine, dihydroxypiperidine, and trihydroxypiperidine, shown below:

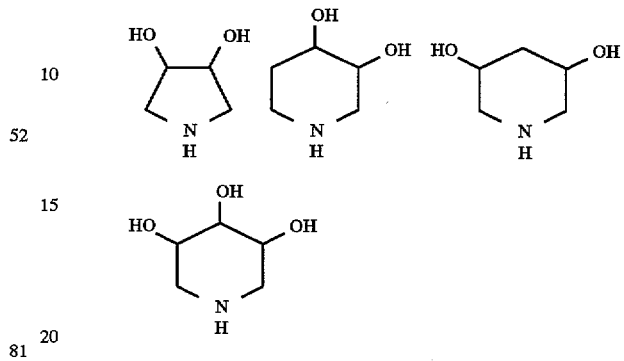

Polyhydroxyl, polyhydroxyalkyl groups, and sugar derivatives such as glucosamine, glucamine, gluconic acid chloride, and tosylate are currently preferred compounds to derivatize and solubilize iodinated carboranes and boranes within the scope of the present invention. Shown below are 1,3,4,6-Tetra-O-Acetyl-D-Glucosamine (HCl),

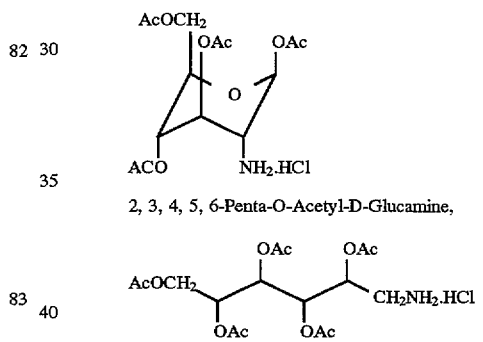

2, 3, 4, 5, 6-Penta-O-Acetyl-D-Glucamine,

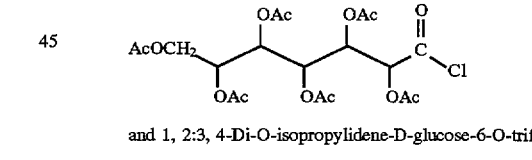

2, 3, 4, 5, 6, 7-Hexa-O-Acetyl-D-Glucoheptonyl Chloride,

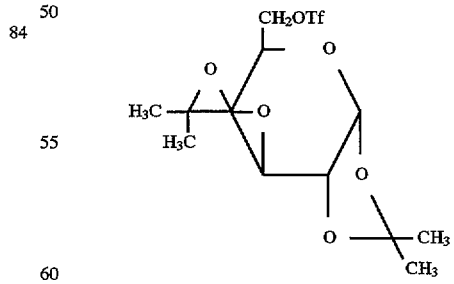

and 1, 2:3, 4-Di-O-isopropylidene-D-glucose-6-O-triflate.

The borane compounds within the scope of the present invention may have symmetrical or unsymmetrical substitution of functional groups. The percentages of iodine are very high for all of the illustrated compounds such that further modification would still allow one to obtain compounds with high percentages of iodine. Dimeric dodecaborane compounds can easily be obtained and could have even higher percentages of iodine per molecule.

The following examples are offered to further illustrate the present invention. These examples are intended to be purely exemplary and should not be viewed as a limitation on any claimed embodiment. All chemicals purchased from commercial sources were analytical grade or better and were used without further purification unless noted.

Silica gel chromatography was conducted with 70–230 mesh 60 Å silica gel (Aldrich Chemical Co.). $^1$H, $^{13}$C, and $^{11}$B NMR were obtained on either a Varian VXR-300 (300 MHz for $^1$H; 75.4 MHz for $^{13}$C); a Bruker AC-200 (200 MHz for $^1$H; 50.3 MHz for $^{13}$C, 64.2 MHz for $^{11}$B); or a Bruker WM-500 (500 MHz $^1$H and 160.47 MHz for $^{11}$B). $^1$H NMR data are referenced to tetramethylsilane as an internal standard ($\delta$=0.0 ppm), $^{13}$C NMR data are referenced to the center peak of the deuterated solvent, and $^{11}$B NMR data are referenced to $BF_3.OEt_2$ as an external standard ($CDCl_3$, $\delta$=0.0 ppm). IR data were obtained on a Perkin-Elmer 1420 infrared spectro-photometer and refer to absorptions of strong intensity unless otherwise noted for (m) medium intensity or (w) weak intensity.

Mass spectral data (both low and high resolution) were obtained on a VG Analytical (Manchester, England) VG-70 SEQ mass spectrometer with associated 11250J Data System. FAB$^+$ mass spectral data were obtained at 8 kV using a matrix of sodium salt of 3-nitrobenzyl alcohol. FAB$^-$ mass spectral data were obtained at 8 kV in a matrix of thioglycerol. Melting points were obtained on a Melt-Temp II melting point apparatus and are uncorrected.

HPLC separations were obtained on either a Hewlett-Packard quaternary 1050 gradient pumping system with a multiple wavelength UV detector (220, 254 and 280 nm) or a Hewlett-Packard Isocratic system consisting of a 1050 pump, variable wavelength UV detector, and a Hewlett-Packard 1047A refractive index detector. Analyses of the HPLC data were conducted on a Hewlett-Packard Vectra QS/16S computer employing Hewlett-Packard HPLC ChemStation software. HPLC separations were conducted at a flow rate of 1 mL/min on a 5 µm, 125×4 mm C-18 columns (LiChrospher 100 RP-18). Isocratic separations of iodinated 1,2- and 1,7-carboranes were conducted with a mixture of 80% MeOH/20% of a 1% aqueous HOAc solution. Iodination reactions of monocarbon carboranes and 1,12-dicarbaborane (p-carborane) were evaluated on a gradient system using an initial mixture of 60% MeOH/40% of an aqueous 1% HOAc solution. The gradient was held at the initial mixture for 5 minutes, increased to 100% MeOH over a 10 minute period, and held at 100% MeOH for 10 minutes. Retention times (r.t.) for compounds are given in the experimental descriptions. (Note: For consistency, the various salts of the compounds will be labeled as H$^+$=a, Na$^+$=b, Cs$^+$=c, R$_4$N$^+$=d, such that Na$_2$B$_{12}$H$_{12}$ is 2b whereas Cs$_2$B$_{12}$H$_{12}$is 2c.)

EXAMPLE 1

Synthesis of $B_{12}H_{12}^{2-}$, 12

$B_{12}H_{12}^{2-}$ is synthesized according to the procedure described in Miller, H. C. and Muetterties, E. L., "Borane Anions," *Inorganic Synthesis*, vol. 10, pp. 88–91 (1967). In the procedure, 62.5 g, triethylamine-borane (Alfa) is heated in ultrasene solution at 190° C. with 30 g, decaborane (Alfa) over a 20 to 30 minute period. A 79% yield of purified product is obtained (67 g). The reaction is as follows:

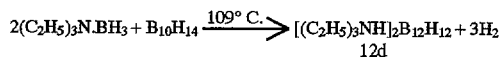

12d

EXAMPLE 2

Synthesis of $(Et_3NH)_2B_{10}H_{10}$

A two neck 1 L round bottom flask equipped with a addition funnel and a reflux condenser was charged with 30 g (0.246 mol) of decaborane in 300 mL of xylene. To this mixture was added 90 mL (0.646 mol) of triethylamine via the addition funnel over a 5 minute period. As soon as the amine was added, a yellow-white precipitate came out of solution. The reaction mixture was heated to approximately 110° C. and stirred for 3 hours. The heating bath temperature was then raised to approximately 170° C. and the reaction mixture was stirred at that temperature for 6 hours. After this time, the reaction mixture was cooled to 0° C. The precipitate was filtered and washed four times with 50 mL portions of isopropyl alcohol (IPA). The IPA washings removed most of the original yellow color. After a final wash with 100 mL of $Et_2O$, the solid was dried under vacuum to yield 76.7 g (97%) of crude product.

The crude product was recrystallized by dissolving in 150 mL of cold (e.g. 15° C.) water and the solid that did not dissolve [$(Et_3NH)_2B_{12}H_{12}$ impurity] was filtered. The mother liquor was heated and approximately 400 mL ethanol was added (until solid became visible). The solution was then cooled to 0° C., filtered, and the collected solid was dried. Initially, 57.84 g (73%) of a white solid was obtained (mp 231°–232° C.). Addition of diethyl ether to the filtrate yielded an additional 8.24 g (10%) of a white solid (mp 231°–232° C.).

Physical data: IR (nujol, cm$^{-1}$) 3040(s), 2450(vs); $^{11}$B NMR ($D_2O$, $\delta$ from $BF_3.OEt_2$ external standard) [$^1$H coupled] −1.23 (d,2 B,J=163 Hz), −30.4 (d,8 B,J=149 Hz).

EXAMPLE 3

Synthesis of nido-7-$(CH_3)_3$N-7-$CB_{11}H_{11}$, 46

To a two neck 1 L flask containing a slurry of 24.4 g (0.2 mol) decaborane in 50 mL of hexane was added a solution of 10.82 g (0.22 mol) NaCN and 8.826 g (0.22 mol) NaOH in 200 mL water over a period of 5 minutes. The mixture was stirred vigorously for 2 hours, during which the bath temperature was maintained near room temperature (i.e., 15°–20° C.) with cold water. The reaction solution was then cooled to 0° C. and 50 mL of concentrated HCl was added over 30 minutes. After the addition was complete, Ar was bubbled through the mixture to rid it of HCN (approximately 30 minutes). The mixture was then placed on a rotary evaporator to remove hexanes and residual HCN. The resultant homogeneous solution was cooled to 0° C. and 160 mL of 15% aqueous NaOH was added over a period of 5 minutes. To the cooled solution was added 88.4 g (0.7 mol) dimethylsulfate over a 40 minute period while maintaining a reaction temperature of 0°–5° C. The reaction mixture was removed from the cooling bath and then stirred for an additional 1 hour. The solid was filtered, washed 2× with 150 mL water, then washed with 100 mL 50% EtOH/$H_2O$, and dried under vacuum (0.3 mm/25° C.) to yield 37.25 g (97% based on decaborane) of a white solid.

EXAMPLE 4

Synthesis of closo-1-$(CH_3)_2$NH-1-$CB_{11}H_{11}$, 47

To a three neck 250 mL flask equipped with a reflux condenser and dropping funnel was added 28.6 g (0.15 mol)

of crude nido-7-$(CH_3)_3$N-7-$CB_{11}H_{11}$, 46, prepared in Example 3. To the solid was added 53 mL of $Et_3NBH_3$ dropwise over 5 minutes under Ar. The temperature of the reaction mixture was then (gradually) raised to 205° C., during which time the solid dissolved leaving a light yellow homogeneous solution. The solution was heated for 8 hours with the bath at 205° C. under Ar. After 8 hours at reflux, the $Et_3N$ was distilled from the mixture (23 mL obtained) with the bath temperature as 220° C. The reaction mixture set at room temperature overnight, then 150 mL of MeOH was added, followed by 45 mL of concentrated HCl. The reaction mixture was heated to reflux for 6 hours, then allowed to cool to room temperature. To the cooled solution was added 450 mL of water. Following this the volatile materials were removed on a rotary evaporator. An oily solid was filtered, and the filtrate was washed with 50 mL hot water (75° C.). The remaining solid was stirred in 100 mL 10% aqueous NaOH and filtered. This process was repeated two additional times and the remaining solid was discarded. Acidification of the combined filtrates with concentrated HCl resulted in a voluminous white precipitate which was filtered and dried under vacuum (0.3 mm/25° C.) to yield 14.62 g (52.3% based on decaborane), top. 256°–260° C.

Physical data: IR (nujol, $cm^{-1}$) 3615(s), 3545(s), 2715(s), 2540(vs), 1600(s), 1405(s), 1195(s), 1155(m), 1115(w), 1020(s), 950(w), 930(s), 855(w), 800(m, shoulder at 820); $^{11}B$ NMR (acetone-$d_6$, δ from $BF_3.OEt_2$ external standard) [$^1H$ coupled] −7.48 (d,1 B,J=139 Hz), −12.85 (d,5 B,J=143 Hz), −14.86 (d,5 B,J=155 Hz).

Examples 5–10 illustrate the synthesis of mono and disubstituted decaborane and dodecaborane cages.

EXAMPLE 5

Synthesis of $B_{12}H_{10}(CO_2H)_2^{2-}$, 14 and $B_{12}H_{10}(CO)_2^{2-}$, 15

$B_{12}H_{10}(CO_2H)_2^{2-}$, 14 and $B_{12}H_{10}(CO)_2^{2-}$, 15 are prepared by carbonylation of $B_{12}H_{12}^{2-}$ according to the procedure described by Knoth et al., "Chemistry of Boranes. XIX. Derivative Chemistry of $B_{10}H_{10}^{2-}$ and $B_{12}H_{12}^{2-}$," *Journal of the American Chemical Society*, vol. 89, pp. 4842–4850 (1967). Synthetic procedures for carbonylation result in formation of the dicarboxylic acid as shown in the following reaction sequence.

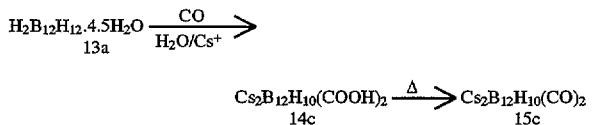

The starting borate acid 13a is prepared from the tetraethylammonium salt 13b by running it over an ion exchange column ($H^+$ form). While the yield of 14c is not high (38%), the reaction can be run on large enough scale to make it a useful preparative method. Special pressure equipment is needed for this reaction. Dehydration at elevated temperatures produces the carbonylated derivative 15, which reacts with various reagents in a manner similar to an acid anhydride.

EXAMPLE 6

Synthesis of $Cs_2B_{10}H_9COOH$

A 1 L two neck flask equipped with an argon balloon and septa was charged with 10.56 g (32.8 mol) of $(Et_3NH)_2B_{10}H_{10}$ and 400 mL of freshly distilled (from $CaH_2$) methylene chloride. This solution was cooled to −10° to −15° C. using dry-ice in a 20% aqueous $CaCl_2$ solution. To the cooled solution (suspension) was added 17.5 mL (35mmol) of a 20% solution of oxalyl chloride in methylene chloride via syringe. The reaction mixture was stirred and allowed to come to room temperature over a 4 hour period. The methylene chloride was removed on a rotoevaporator, then under high vacuum to yield an oily mass. The oily residue was dissolved in 60 mL of water and 60 mL of a 0.5N NaOH solution was added. The resulting clear solution was passed through a $H^+$ ion exchange column (150 g of Amberlite IR-120 in a 1 inch by 14 inch column). An additional 200 mL of water was passed through the column. The eluant (300 mL) was reduced in volume to approximately 40 mL on a heating plate. To the aqueous solution was added 16.57 g (98.4 mmol) of CsCl in 10 mL of water. The solution was then cooled to 5° C. and filtered through a pad of celite to give a clear solution. After rinsing with 20 mL water, the resultant 70 mL aqueous solution was diluted with 140 mL EtOH. The precipitate was collected and dried to give 7.52 g (54%) of a light yellow solid.

IR (nujol, $cm^{-1}$) 2460(s), 1698(m), 1260(w); $^{11}B$ NMR (acetone-$d_6$, δ from $BF_3.OEt_2$ external standard) [$^1H$ coupled] −0.5(1B), −1.3(1B), −25.5(1B), −28.6(3B), −20.6 (4B).

EXAMPLE 7

Synthesis of $B_{12}H_{10}(CH_2NHAc)_2^{2-}$, 19

The bis-(1,12)-acetylaminomethyldecahydrododecaborate(−2) salts are prepared by the reactions shown below. Reaction of 15 with $LiBH_4$ produces the alcohol 16. Conversion of 16 to the bromomethyl derivative 17 is accomplished by reaction with HBr. Conversion of 17 to the methylammonium derivative 18 is accomplished by reaction with ammonia. The acetyl derivative 19 is prepared by reaction of 18 with acetic anhydride and sodium acetate.

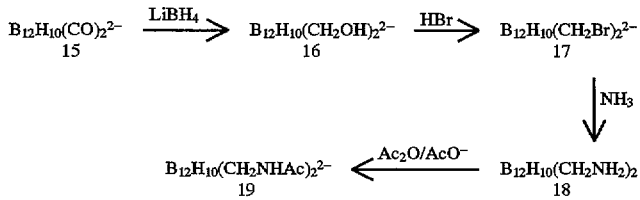

EXAMPLE 8

Synthesis of $B_{12}H_{10}(CH_2NMe_2)_2^{2-}$, 20

The bis-(1-12)-dimethylaminomethyldecahydrododecaborate(–2) salts 20 are prepared by reaction of dimethylamine with the bromomethyl derivative 17 as shown below.

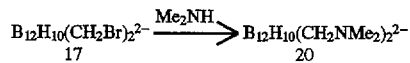

EXAMPLE 9

Synthesis of $B_{12}H_{10}(CH_2CO_2H)_2^{2-}$, 22

The bis-carboxymethyldecahydrododecaborate(–2) salts are prepared by reaction of cyanide ion with 17 to form the cyanomethyl intermediate, 21, followed by hydroxide ion hydrolysis as described in Knoth W. H., "Chemistry of Boranes. XXXI. 1,10-Bis(hydroxymethyl) octachlorodecaborate(2–)," *Journal of the American Chemical Society*, vol. 89, pp. 4850–4852 (1967).

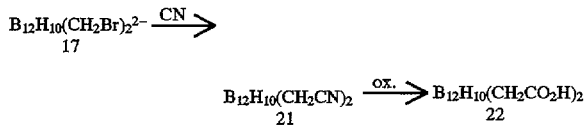

EXAMPLE 10

Synthesis of $CsB_{12}H_{11}NH_3$, 40

To a 250 mL round bottom flask containing 100 mL of water was added 10.0 g (24.5 mmol) of $Cs_2B_{12}H_{12}$. The mixture was heated to boiling, which resulted in a homogeneous solution being formed. To the hot solution was added 5.23 g (47.1 mmol) of hydroxylaminesulfonic acid, and the mixture was heated at reflux for 8 hours. The water was removed on a rotary evaporator and the residue was dried. To the residue was added 5 mL of acetone followed by 5 mL of water. The solid was filtered, washed 2×10 mL EtOH, and dried under vacuum (0.3 mm/12 hours) to give 10.72 g of a white solid.

IR (nujol, cm$^{-1}$) 3560(s), 3240(s), 2480(vs), 1245(m), 1205(w), 1075(s), 1055(s), 1025(s), 855(w), 720(s), 710(m); $^{11}$B NMR (acetone-d$_6$, δ from $BF_3 \cdot OEt_2$ external standard) [$^1$H decoupled] –6.69(s,1 B), –16.27(d,10 B,J=111 Hz), –19.89 (d,1 B,J=139 Hz).

Periodination of disubstituted borane cage compounds. One approach to periodinate disubstituted borane cage compounds is to form the derivatized borate salts first, and then iodinate them. This approach is preferred for those compounds which do not contain functional groups that readily react with electrophilic iodine. A description of this chemistry is given below.

Another approach is to iodinate the dicarboxylate salt 15, as depicted below, and then perform the substituent conversion reactions described previously. For example, Knoth et al., "Chemistry of Boranes. XXX. Carbonyl Derivatives of $B_{10}H_{10}^{2-}$ and $B_{12}H_{12}^{2-}$," *Journal of the American Chemical Society*, vol. 89, pp. 4842–4850 (1967), report that the reaction of 15c with ICl in refluxing tetrachloroethane for 18 hours gave an 81% yield of the desired iodinated compound 16. Passage of the iodinated cesium salt over an acidic ion exchange column followed by evaporation and sublimation of the solid yielded the dehydrated periodinated dicarbonyl derivative 17 as shown below.

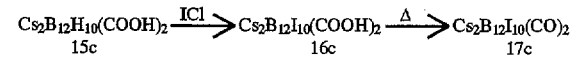

The periodinated compound 1,10-$B_{10}I_8(N_2)$ was prepared from 1,10-$B_{10}I_8(NH_3)_2$ in 94% yield by reaction with sodium nitrite in acetic acid according to the procedure described by Knoth W. H., "Chemistry of Boranes. XXVI. Inner Diazonium Salts 1,10-$B_{10}H_8(N_2)_2$, $B_{10}Cl_8(N_2)_2$, and $B_{10}I_8(N_2)_2$," *Journal of the American Chemical Society*, vol. 88, pp. 935–939 (1966). The isocyanate derivatives $Cs_2B_{10}I_8(NCO)_2$ and $Cs_2B_{12}I_{10}(NCO)_2$ were prepared from the corresponding borane carbonyl compounds (e.g. 17c) by reaction with $NaN_3$ according to the procedure described by Knoth et al., "Chemistry of Boranes. XXX Carbonyl Derivatives of $B_{10}H_{10}^{2-}$ and $B_{12}H_{12}^{2-}$," *Journal of the American Chemical Society*, vol. 89, pp. 4842–4850 (1967).

EXAMPLE 11

Synthesis of $Cs_2B_{12}I_{12}$, 5c $Cs_2B_{12}I_{12}$ is synthesized according to the procedure described by W. H. Knoth et al., "Chemistry of Boranes. IX. Halogenation of $B_{10}H_{10}^{-2}$ and $B_{12}H_{12}^{-2}$," *Inorganic Chemistry*, vol. 3, pp. 159–167, (1964). A 250 mL three neck round bottom flask equipped with a dropping funnel and a reflux condenser was charged with 5 g (12.3 mmol) of $Cs_2B_{12}H_{12}$ 2c in 100 mL of $CCl_4$. To this mixture was added 6.85 g (27.0 mmol) of iodine. The reaction mixture was stirred at room temperature for 30 minutes and a solution 27.9 g (171.5 mmol) iodine monochloride in 10 mL $CCl_4$ was added dropwise over 15 minutes. The reaction mixture was heated to reflux for 48 hours, allowed to cool to room temperature, and filtered. The solid mass was washed with methylene chloride (5×50 mL) to remove the unreacted iodine/iodine monochloride. A total of 14.23 g (61%) of crude yellow solid was obtained. The crude solid was dissolved in 300 mL boiling water and allowed to cool (15° C.). The precipitate was collected by filtration and dried (15° C./0.15 torr) to yield 8.2 g (35%) of white shiny crystals. The volume of the filtrate was reduced to 100 mL by boiling, and upon cooling to 15° C. and filtration/drying, an additional 3.80 g (16%) of the product was obtained.

A 6.00 g quantity of the isolated solid was recrystallized by dissolving in 90 mL of boiling water. After cooling to room temperature, filtering, and drying, 5.61 g (93.4%) of a white solid was isolated (mp>380° C.).

Physical properties: IR (nujol, cm$^{-1}$) 940(s), 925(s); $^{11}$B NMR (acetone-d$_6$, δ, $BF_3 \cdot OEt_2$ external standard) –15.52 [for both $^1$H coupled and decoupled spectra]; FAB$^+$ Mass Spectra for $Cs_2B_{12}I_{12}$ [M$^+$: calculated 1919 (100%); found 1919 (100%) with appropriate boron isotope envelope], [also found M$^+$18 ($H_2O$); 1937 (100%)].

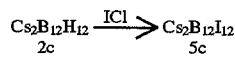

EXAMPLE 12

Preparation of $Na_2B_{12}I_{12}$

One gram of $Cs_2B_{12}I_{12}$ from Example 11 was dissolved in 150 mL of hot water (65° C.) and was passed over a preheated (70° C.) 8¾ inch by ¾ inch (filled volume) column packed with Amberlite IR-120 plus ion-exchange resin, sodium salt. A second addition of 100 mL of hot water (80° C.) was passed over the column. [Analysis of the eluted water solution by UV (268 nm) indicated that a 107% recovery was obtained.] The aqueous solution (250 mL) was concentrated on a hot plate to approximately 20 mL. This solution was then further concentrated under vacuum on a rotoevaporator to yield a solid. Drying of the light tan solid under high vacuum gave 0.89 g (100%) of material. This solid was soluble in 1.5 mL of water at room temperature.

EXAMPLE 13

Synthesis of $B_{12}I_{10}(CN_2NHAc)_2^{2-}$, 6; $B_{12}I_{10}(CH_2NMe_2)_2^{2-}$, 7; and $B_{12}I_{10}(CH_2CO_2H)_2^{2-}$, 8

$B_{12}I_{10}(CN_2NHAc)_2^{2-}$, 6; $B_{12}I_{10}(CH_2NMe_2)_2^{2-}$, 7; and $B_{12}I_{10}(CH_2CO_2H)_2^{2-}$, 8 are prepared substantially according to the procedure of Example 11. The reactions are shown below.

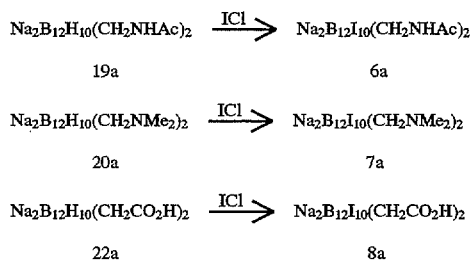

EXAMPLE 14

Synthesis of $Cs_2B_{10}I_{10}\cdot CsI$

A 500 mL round bottom flask equipped with a addition funnel and a reflux condenser was charged with 10 g (31 mmol) of $(Et_3NH)_2B_{10}H_{10}$ in 200 mL of methanol. To this solution was added 39.40 g (155 mmol) of iodine and the resulting mixture was stirred at room temperature for 30 minutes. Then, 60.5 g (372 mmol) of iodine monochloride in 50 mL of methanol was added via the dropping funnel over a 30 minute period. The reaction mixture was refluxed for 8 hours (bath temperature 80° C.). The solvent was then removed by distillation with heating to 100° C. To the residue was added 150 mL of a 10% aqueous solution of NaOH. This mixture was stirred well and was filtered. A 18.28 g (108.6 mmol) quantity of CsCl in 25 mL water was added to the filtrate. The solvent was then removed on a rotoevaporator and the iodinated product was extracted using 2×50 mL of acetone. The product was triturated from the acetone by addition of 300 mL hexane to yield 42.4 g (71.8%) of a brown solid.

The crude product was recrystallized by dissolving it in 250 mL boiling water. After cooling to approximately 15° C., 18.3 g (43.2%) of a faint yellow solid was isolated. An additional 15.0 g (35.3%) of a white shiny crystalline solid was isolated after reducing the volume by boiling off the water. The volume was further reduced by boiling and upon cooling to room temperature an additional 3.0 g (7.1%) of a white solid was obtained. The white solid had a melting point >380° C.

Physical data: IR (nujol, cm$^{-1}$) 1080(m, shoulder at 1100), 930(s, shoulder at 945), 820(m); $^{11}$B NMR (acetone-$d_6$, δ, $BF_3\cdot OEt_2$ external standard) [$^1$H coupled] −2.10 (s,2 B), −19.32(s,8 B), [$^1$H uncoupled same as coupled]; FAB$^+$ Mass Spectra.

EXAMPLE 15

Conversion of $Cs_2B_{10}I_{10}\cdot CsI$ to $Cs_2B_{10}I_{10}$

A 10 g quantity (5.3 mmol) of $Cs_2B_{10}I_{10}\cdot CsI$ in 100 mL of hot water (approximately 85° C.) was passed through a preheated ion exchange column (H$^+$ form; 30 g Amberlite IR-120 plus). An additional 100 mL of hot water was eluted through the column. The aqueous solution was boiled to reduce its volume to 50 mL. During the boiling process, a stream of argon gas was passed through the solution to remove dissolved HI. After cooling to room temperature, 2 g (12 mmol) of CsCl in 3 mL water was added to the aqueous solution. Filtration and drying of the precipitate under vacuum yielded 5.82 g (67%) of white solid $Cs_2B_{10}I_{10}$. Reduction of the filtrate solution to 20 mL yielded an additional 1.73 g (20%) of white solid.

Recrystallization was accomplished from water. A 1 gram quantity of compound was dissolved in 8 mL of boiling water. Allowing the water to cool to room temperature gave a quantitative yield of dicesium salt.

EXAMPLE 16

Preparation of $Na_2B_{10}I_{10}$

One gram of $Cs_2B_{10}I_{10}$ from Example 15 was dissolved in 100 mL of hot water (60° C.) and was passed over a preheated (70° C.) 8¾ inch by ¾ inch (filled volume) column packed with Amberlite IR-120 plus ion-exchange resin, sodium salt. A second addition of 100 mL of hot water (80° C.) was eluted immediately following the first elution. [Analysis of the eluted water solution by UV (241 nm) indicated that a 96% recovery was obtained.] The aqueous solution (200 mL) was concentrated on a hot plate to approximately 20 mL, and then taken to dryness under vacuum on a rotoevaporator. Drying of the light tan solid under high vacuum gave 0.87 g of material. This solid was easily solubilized in 1.5 mL of water at room temperature.

EXAMPLE 17

Synthesis of $Cs_2B_{10}I_9COOH$

A 250 mL three neck round bottom flask equipped with a reflux condenser and an addition funnel was charged with 2.55 g (5.96 mmol) of $Cs_2B_{10}H_9COOH$ and 80 mL of tetrachloroethane. To the resulting suspension, 4.26 g (16.8 mmol) of iodine was added. This solution was stirred for 1.5 hours, and a solution containing 12.18 g (75 mmol) of iodine monochloride in 20 mL of tetrachloroethane was added via the addition funnel. The reaction mixture was heated to 150° C. and was stirred at that temperature for 18 hours. The reaction mixture was then cooled to room temperature and the solid was filtered. The filtered solid was washed with 3×25 mL of methylene chloride to give 7.79 g (84%) of a yellow-brown solid.

The solid was purified by dissolving in 20 mL water, boiling and adding Zn dust portionwise until the solution became colorless. The solution was filtered hot and was reduced in volume to 10 mL. After cooling to room temperature, the solution was cooled slowly to 0° C. and 6.12 g (78.6%) of a colorless solid was isolated.

Physical data: IR (nujol, cm$^{-1}$)3600-3300 (w), 1680(s), 1595(s), 1270(s), 1165(w), 1080(s, shoulder at 1100), 930(s, shoulder at 945), 880(m), 830(m), 770(m), 720(s); $^{11}$B NMR (acetone-$d_6$, δ, $BF_3\cdot OEt_2$ external standard, 500 MHz) [$^1$H decoupled] −0.9, −4.0, −18.3, −19.7, −21.47 (note: the resonances are not resolved in −15 to −26 ppm region, and small peaks are seen at 1.0 and −5.1 ppm). FAB⁺ MS [(CH₃)₄N]₂B₁₀I₉CO₂[(CH₃)₄N]: M⁺1 calculated 1518, found 1518 (100%) with appropriate isotope envelope.

EXAMPLE 18

Synthesis of $CsB_{12}I_{11}NH_3$, 43

To a three neck round bottom flask equipped with a reflux condenser and a dropping funnel containing 5 g of crude aminoborane 40 from Example 10 in 150 mL of $CCl_4$ was added 10.9 g (43 mmol) of $I_2$. This mixture was stirred at room temperature for 1 hour and 31.11 g (191 mmol) of ICl in 30 mL of $CCl_4$ was added dropwise over 30 minutes. The reaction temperature was raised to 80° C. and the mixture was refluxed for 24 hours. The reaction mixture was then allowed to cool to room temperature, and the solid was filtered. The filtrate was washed with 4×25 mL methylene chloride to give 8.24 g of a dark brown solid. The solid was dissolved in a mixture of 50 mL water and 20 mL acetone with boiling. To the hot mixture was added Zn dust portionwise until the solution became colorless. The hot solution was filtered and reduced in volume to approximately 30 mL. This solution was cooled using an ice-$H_2O$ bath and the precipitate was filtered to give 6.78 g of a white solid. The solid was purified on a silica gel column (4.5×35 cm, 60 Å) eluting with 40% acetone/57% EtOAc/3% HOAc mixture to yield 5.53 g (34.1%) of a white solid, mp. >300° C.

IR (nujol, cm⁻¹) 3640-3300(w), 3180(w), 1590(s), 1400 (m), 920(s, shoulder at 935); ¹¹B NMR (acetone-d₆, δ from BF₃.OEt₂ external standard, 500 MHz) [¹H decoupled] −8.16(s,1 B), −15.23(s,5 B), −16.59(s,6 B). FAB⁺ Mass Spectra for [CH₃)₄N]₂B₁₂I₁₁NH₃ calculated M⁺1=1692, found 1692 (100%) with appropriate boron isotope envelope.

EXAMPLE 19

Preparation of cesium undeca-B-iodocarba-closo-dodecaborane, 51c

A 100 mL round bottom flask was charged with 0.452 g (1.64 mmol) of cesium 1-carba-closo-dodecaborane. To the flask was then added 10 mL tetrachloroethane and 9.58 g (59 mmol) of ICl. A reflux condenser with a $CaCl_2$ drying tube attached was connected to the reaction flask. After stirring the reaction mixture for 30 min at room temperature, it was heated slowly to 150° C. in an oil bath. After 63 hours the reaction mixture was removed from the oil bath and was allowed to come to room temperature. The solid which formed was collected by gravity filtration and was washed with 50 mL $CH_2Cl_2$. The solid was then dissolved in 70 mL EtOAc, washed with 2×20 mL of aqueous $NaHSO_3$, 2×10 mL $H_2O$, and 20 mL saturated aqueous NaCl. The EtOAc solution was then dried over $MgSO_4$, and concentrated on a rotary evaporator to give an oily mass. The oily material was placed on a high vacuum to remove residual solvent yielding 1.52 g (56%) of a faint yellow solid. A 200 mg quantity of the crude product was dissolved in 30 mL of water and was passed through a 2.5×15 cm ion exchange column (Amberlite IR-120 plus). An additional 70 mL of water was passed through the column to assure complete elution. The aqueous eluant was concentrated to approximately 5 mL on a rotary evaporator and a 1:1 w/v solution of CsCl in $H_2O$ was added. The precipitate was gravity filtered and dried at 75° C./0.2 torr to yield 214 mg of a faint yellow solid, mp. >300° C. (turns brown color on heating). HPLC of this solid indicated that the compound (r.t.=12.1 min) was >97% pure.

IR (nujol, cm⁻¹) 1597(w), 1093(m), 915(m), 750(w); ¹H NMR (acetone-d₆) 2.86; ¹¹B NMR (acetone-d₆, 64.21 MHz, decoupled): −7.7(1 B), −12.1 (5 B), −18.9 (5 B) [¹H coupled spectrum identical to decoupled]; FAB⁻ MS (isotopic abundance), Mass calculated for $CHB_{11}I_{11}$: 1526(37%), 1527(74%), 1528(100%), 1529(81%), 1530(30%); Found 1526(36%), 1527(74%), 1528(100%), 1529(82%), 1530 (30%).

EXAMPLE 20

Preparation of 1-amino-undeca-B-iodo-1-carba-Closo-dodecaborane

To a 250 mL cone bottom flask containing 100 mg (0.630 mmol) of 1-amino-undecahydro-1-carba-closo-dodecaborane was added a solution of ICl (1.839 g, 11.3 mmol) in 10 mL of tetrachloroethane. The flask was fitted with a condenser and a CsCl drying tube and was heated to 150°–160° C. for 48 hours. The reaction mixture was then poured into 20 mL of 10% $NaHCO_3$ solution. The solvent was removed on a rotary evaporator to dryness. This material was dissolved in 25 mL $H_2O$ and was passed through a 2.5×18 cm ion exchange column (IR-120 plus, Aldrich). An additional 75 mL of $H_2O$ was added to the eluant and the solvent was removed on a rotary evaporator. The residue was dissolved in 25 mL $H_2O$. The light yellow precipitate was filtered to yield 0.672 g (69%) after drying. The crude product was dissolved in 200 mL hot $H_2O$ and was passed through a preheated 2.5×18 cm ion exchange column (IR-120 plus). An additional 200 mL of hot water (80° C.) was eluted through the column and the combined eluants were concentrated on a rotary evaporator to approximately 30 mL volume. To this material was added 1 g of Zn dust, followed by heating to 80° C. and filtration through a celite pad. An additional 20 mL of hot water was used to rinse the celite pad and the water was removed on a rotary evaporator to yield 0.541 g (55.7%) of a light yellow solid (after drying under vacuum). HPLC indicated that the compound (r.t.=9.4 min) was >98% pure, mp. 300° C. IR (nujol, cm⁻¹) 3600(w), 1690(w), 1595(m), 935, 720(w); ¹¹B NMR (acetone-d₆) −11.8 (1 B), −14.8 (10 B) [¹H coupled spectrum same as decoupled spectrum].

EXAMPLE 21

Preparation of 4,5,6,8,9,10,11,12-octa-B-iodo-1,7-dicarba-closo-dodecaborane A 100 mL three neck round bottom flask was charged with 1.0 g (6.93 mmol) of 1,7-carborane (Astor LTD, Los Angeles (formerly Consumer Health Products)). The flask was purged with argon and 11 mL (124 mmol) of triflic acid was added. Following this 11 mL (40.4 g, 249 mmol) of ICl was carefully added. After stirring the reaction mixture at room temperature for 10 min, the reaction temperature was elevated to 120° C. for 6 days. The reaction mixture was allowed to cool to room temperature and 20 mL of ice-cold $H_2O$ was added to the mixture. A 70 mL quantity of 15% aqueous $NaHSO_3$ was added to quench the excess ICl. The precipitate in the yellow solution was collected by filtration to yield 5.52 g of a light brown solid. The solid was dissolved in 200 mL hot EtOAc (60° C.) and zinc dust was added portionwise until the solution became colorless. The colorless solution was passed through a pad of celite and was concentrated on a rotary evaporator. The resultant white solid was dried under vacuum to yield 4.9 g (50%).

A small portion of the crude compound (84% pure by HPLC) was recrystallized from methanol/acetone to give a colorless solid, mp. >300° C. HPLC indicated that this compound (r.t.=8.0 min) was 97% pure (RI detection). IR (nujol, cm$^{-1}$) 3000(m), 1133(m), 1109(w), 953(m), 902,882 (w), 840(m), 788(w); $^1$H NMR (DMSO-d$_6$) 7.67 (s, 2 H), 6.43 (s, 2 H); $^{13}$C NMR (DMSO-d$_6$) 63.95, $^{11}$B NMR (acetone-d$_6$) −9.20 (3 B), −11.01 (2 B), −19.69 (5 B) [no noticeable difference in $^1$H couple$_d$ spectrum]; MS/HRMS (FAB$^-$, isotopes); Mass calculated for C$_2$H$_4$B$_{10}$I$_8$: 1148 (29%), 1149 (66%), 1150 (100%), 1151.3560 (90%), 1152.3523 (38%); Found: 1148 (27%), 1149 (64%), 1150 (100%), 1151.3508 (98%), 1152.3481 (48%).

EXAMPLE 22

Preparation of 4,5,7,8,9,10,11,12-octa-B-iodo-1,2-dicarba-closo-dodecaborane

This compound was prepared as described in Example 21 (above). The reaction of 1.0 g (6.93 mmol) of 1,2-carborane (Astor LTD, Los Angeles (formerly Consumer Health Products)) yielded 5.28 g (66%) of a light yellow solid. A 300 mg quantity of the crude solid was recrystallized form 10 mL of a 1:1 mixture of acetone/MeOH to yield 207 mg (67%) of a colorless solid, mp. >300° C. HPLC indicated that this compound (r.t.=9.7 min) was 95% pure (RI detection). IR (nujol, cm$^{-1}$) 3033(m), 2995(m), 1179(m), 1108(m), 953(m), 911, 890(w), 860(m), 798(m); $^1$H NMR (DMSO-d$_6$) 7.61 (s, 2 H), 6.40 (s, 2 H); $^{13}$C NMR (DMSO-d$_6$) 61.53, $^{11}$B NMR (acetone-d$_6$) −4.03 (2B0, −12.52 (4 B), (broad shoulder at −10) −20.09 (4 B) [shoulder at −9 to −11 ppm splits in $^1$H coupled spectrum]; MS (FAB$^-$, isotopes); Mass Calculated for C$_2$H$_4$B$_{10}$I$_8$: 1148 (29%), 1149 (66%), 1150 (100%), 1151 (90%) 1152 (38%); Found: 1148 (27%), 1149 (60%), 1150 (100%), 1151 (100%) 1152 (49%).

EXAMPLE 23

Preparation of dodeca-iodo-1,12-dicarba-closo-dodecaborane

This compound was prepared as described in Example 21 (above). The reaction of 1.0 g (6.93 mmol) of 1,12-carborane (Astor LTD, Los Angeles) yielded 9.12 g (79%) of a light brown solid after drying under vacuum. A 100 mg quantity of this solid was purified by washing with (1:1) MeOH/acetone to give 89 mg of a white solid. mp. >300° C. IR(nujol, cm$^{-1}$) 1112, 905 (with shoulder at 920), 850(w), 720 (w); $^{11}$B NMR (THF, BF$_3$.OEt$_2$ in benzene-d$_6$ external standard) −16.9 (s) [no noticeable difference in $^1$H-coupled spectrum]; MS (FAB$^-$, isotopes); Calculated for C$_2$B$_{10}$I$_{11}^-$: 1526 (9%), 1527 (29%), 1528 (66%), 1529 (100%), 1530 (90%), 1531 (37%); Found: 1526 (14%), 1527 (37%), 1528 (73%), 1529 (100%), 1530 (88%), 1531 (32%).

Diagnostic compositions. The XRCM compounds of this invention are preferably formulated into diagnostic compositions for enteral or parenteral administration. The XRCM formulations may contain conventional pharmaceutical carriers and excipients appropriate for the type of administration contemplated.

For example, parenteral formulations for X-ray imaging advantageously contain a sterile aqueous solution or suspension of an iodinated borane cage molecule X-ray contrast agent according to this invention. Various techniques for preparing suitable pharmaceutical solutions and suspensions are known in the art. Such solutions also may contain pharmaceutically acceptable buffers, stabilizers, antioxidants, and electrolytes, such as sodium chloride. Parenteral compositions may be injected directly or mixed with a large volume parenteral composition for systemic administration.

Formulations for enteral administration may vary widely, as is well-known in the art. In general, such formulations include a diagnostically effective amount of a XRCM in an aqueous solution or suspension. Such enteral compositions may optionally include buffers, surfactants, adjuvants, thixotropic agents, and the like. Compositions for oral administration may also contain flavoring agents and other ingredients for enhancing their organoleptic qualities.

The diagnostic compositions within the scope of the present invention are administered in doses effective to achieve the desired enhancement of the X-ray image. Such doses may vary widely, depending upon the degree of iodination, the organs or tissues which are the subject of the imaging procedure, the X-ray imaging equipment being used, etc. Typical total dosage amounts of the diagnostic compositions are in the range from about 320 to about 600 mg I/kg body weight. Those skilled in the art will appreciate that it is common to administer the total dosage amount through several lower dosage administrations. The concentration of such diagnostic compositions is preferably in the range from about 160 mg I/mL to about 350 mg I/mL.

The diagnostic compositions of this invention are used in a conventional manner in X-ray. Compositions may be administered in a sufficient amount to provide adequate visualization, to a mammal either systemically or locally to an organ or tissues to be imaged, and the animal then subjected to the X-ray procedure. The compositions enhance the X-ray images obtained by these procedures.

From the foregoing, it will be appreciated that the present invention provides iodinated diagnostic X-ray contrast media possessing high percentages of iodine by weight, but which also have good solubility and low osmolality.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for obtaining X-ray images of body organs and tissues which comprises:

(a) administering to a mammal, a diagnostically effective amount of a stable, highly iodinated borane cage compound in a pharmaceutically acceptable carrier, said stable iodinated borane cage compound having a general formula:

wherein B$^{cm}$ is a stable borane cage moiety containing from 9 to 12 boron atoms in either a closo- or nido- structure and optionally containing up to 3 carbon atoms which replace boron atoms as part of the cage structure; I represents iodine atoms of x number substituted on boron atoms of B$^{cm}$ and x is from 6 to 11; and R is a substituent of either a boron atom or carbon atom of B$^{cm}$ which contains functional groups that alter the overall charge or solubility of the stable iodinated borane cage compound and y is from 1 to 6; and z represents the overall charge of the stable iodinated borane cage compound ranging from −4 to +4; and (b) obtaining X-ray images of the organs and tissues.

2. The method for obtaining X-ray images as defined in claim 1, wherein $B^{cm}$ is a closo-decaborane cage moiety and the stable iodinated borane cage compound is $B_{10}I_{10-n}R_n$ where n is from 1 to 4.

3. The method for obtaining X-ray images as defined in claim 1, wherein $B^{cm}$ is a closo-carbanonaborane cage moiety and the stable iodinated borane cage compound is $CB_9I_{9-n}R_{n+1}$ where n is from 0 to 3.

4. The method for obtaining X-ray images as defined in claim 1, wherein $B^{cm}$ is a closo-dicarbaoctaborane cage moiety and the stable iodinated borane cage compound is $C_2B_8I_{8-n}R_{n+2}$ where n is from 0 to 2.

5. The method for obtaining X-ray images as defined in claim 1, wherein $B^{cm}$ is a closo-dodecaborane cage moiety and the stable iodinated borane cage compound is $B_{12}I_{12-n}R_n$ where n is from 1 to 6.

6. The method for obtaining X-ray images as defined in claim 5, wherein R is selected from —CH$_2$NHCOCH$_3$, —CH$_2$N(CH$_3$)$_2$, —CH$_2$CO$_2$H, —N(CH$_3$)$_2$, —NHCO(CHOH)$_5$CH$_2$OH, or

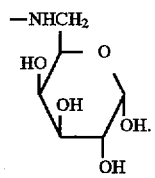

7. The method for obtaining X-ray images as defined in claim 5, wherein R is selected from —NHCH$_2$COOH, —NHCH$_2$CONHCH$_2$(CHOH)$_4$CH$_2$OH, or

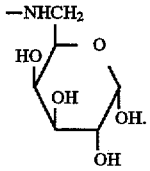

8. The method for obtaining X-ray images as defined in claim 1, wherein $B^{cm}$ is a closo-carbaundecaborane cage moiety and the stable iodinated borane cage compound is $CB_{11}I_{11-n}R_{n+1}$ where n is from 0 to 5.

9. The method for obtaining X-ray images as defined in claim 8, wherein n is 0.

10. The method for obtaining X-ray images as defined in claim 8, wherein R is selected from —NHCO(CHOH)$_5$CH$_2$OH, —NHCH$_2$COOH, —NH$_2$ or

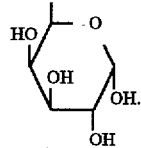

11. The method for obtaining X-ray images as defined in claim 1, wherein $B^{cm}$ is a closo-dicarbadecaborane cage moiety and the stable iodinated borane cage compound is $C_2B_{10}I_{10-n}R_{n+2}$ where n is from 0 to 4.

12. The method for obtaining X-ray images as defined in claim 11, wherein the two cage carbon atoms are ortho (1,2-) to one another in the closo cage structure.

13. The method for obtaining X-ray images as defined in claim 12, wherein R is selected from —CH$_2$CHOHCH$_2$OH or

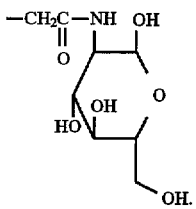

14. The method for obtaining X-ray images as defined in claim 11, wherein the two cage carbon atoms are meta (1,7-) to one another in the closo cage structure.

15. The method for obtaining X-ray images as defined in claim 14, wherein R is selected from —CONHCH$_2$(CHOH)$_4$CH$_2$OH or —CH$_2$NHCO(CHOH)$_5$CH$_2$OH.

16. The method for obtaining X-ray images as defined in claim 11, wherein the two cage carbon atoms are para (1,12-) to one another in the closo cage structure.

17. The method for obtaining X-ray images as defined in claim 1, wherein $B^{cm}$ is a nido-carbadecaborane cage moiety and the stable iodinated borane cage compound is $CB_{10}I_{10-n}R_{a+1}H$ where n is from 0 to 3.

18. The method for obtaining X-ray images as defined in claim 1, wherein $B^{cm}$ is a nido-dicarbanonaborane cage moiety and the stable iodinated borane cage compound is $C_2B_9I_{9-n}R_{n+2}H$ where n is from 0 to 3.

19. The method for obtaining X-ray images as defined in claim 18, wherein the two cage carbon atoms are ortho (1,2-) to one another in the nido cage structure.

20. The method for obtaining X-ray images as defined in claim 18, wherein the two cage carbon atoms are meta (1,3-) to one another in the nido cage structure.

21. The method for obtaining X-ray images as defined in claim 1, wherein R is selected from hydrogen, amine, alkyl amine, dialkyl amine, trialkyl amine, carboxylate, alkylcarboxylate, alcohol, alkyl alcohol, ester, alkyl ester, or combinations thereof.

22. The method for obtaining X-ray images as defined in claim 1, wherein R is selected from cyclic heteroalkyl polyalcohol or acyclic heteroalkyl polyalcohol groups, which R group is attached to the stable iodinated borane cage compound through a boron-carbon, carbon-carbon, boron-nitrogen, carbon-nitrogen, boron-oxygen, or carbon-oxygen bond.

23. The method for obtaining X-ray images as defined in claim 1, wherein R is a heterocyclic amino-alcohol, polyhydroxyl group, polyhydroxyalkyl group, or sugar derivative, which R group is attached to the stable iodinated borane cage compound through a boron-carbon, carbon-carbon, boron-nitrogen, carbon-nitrogen, boron-oxygen, or carbon-oxygen bond.

24. The method for obtaining X-ray images as defined in claim 1, wherein the stable iodinated borane cage compound has a negative overall net charge, z, and the stable iodinated borane cage compound further comprises a positively charged counterion selected from Na ions, K ions, Ca ions, alkyl amines, alkylamino alcohols, aminopolyalcohols; or mixtures thereof.

25. The method for obtaining X-ray images as defined in claim 1, wherein the stable iodinated borane cage compound has a positive overall net charge, z, and the stable iodinated borane cage compound further comprises a negatively charged counterion selected from alkyl acids, hydroxyalkyl acids, polyhydroxyalkyl acids, or mixtures thereof.

* * * * *